United States Patent [19]

Koike et al.

[11] Patent Number: 4,851,387
[45] Date of Patent: Jul. 25, 1989

[54] 5-SUBSTITUTED AMINO-4-HYDROXY-PENTANOIC ACID DERIVATIVES AND THEIR USE

[75] Inventors: Yutaka Koike, Koshigaya; Masato Nakano, Tokyo; Shugo Atsuumi, Tokyo; Seiichi Tanaka, Tokyo; Hajime Morishima, Tokyo; Kenji Matsuyama, Kashiwa, all of Japan

[73] Assignee: Banyu Pharmaceutical Co., Ltd., Tokyo, Japan

[21] Appl. No.: 106,804

[22] Filed: Oct. 13, 1987

[30] Foreign Application Priority Data

Oct. 14, 1986 [JP] Japan ................................ 61-242124
Sep. 23, 1987 [JP] Japan ................................ 62-237994

[51] Int. Cl.$^4$ ........................ A61K 37/43; C07K 5/06; C07K 5/08; C07K 5/10; C07D 233/64; C07C 125/06; C07C 103/19; C07C 103/00; C07C 103/20
[52] U.S. Cl. ......................................... 514/17; 514/18; 514/19; 530/323; 530/330; 530/331; 530/332; 548/344; 560/159; 564/157; 564/158; 564/152; 564/153
[58] Field of Search ............... 530/330, 331, 323, 332; 514/17, 18, 19; 548/344; 560/159; 564/157, 158, 152, 153

[56] References Cited

U.S. PATENT DOCUMENTS 4,729,985 3/1988 Kleinman et al. .................... 514/17

FOREIGN PATENT DOCUMENTS 0045665 2/1982 European Pat. Off. ............ 530/328

Primary Examiner—Delbert R. Phillips
Attorney, Agent, or Firm—Oblon, Spivak, McClelland, Maier & Neustadt

[57] ABSTRACT

A 5-substituted amino-4-hydroxy-pentanoic acid derivative having the formula:

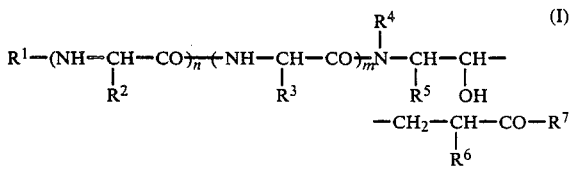

wherein $R^1$ is a hydrogen atom or an N-protecting group, $R^2$, $R^3$ and $R^5$ may be any of a variety of groups including the side chains of amino acid residues, $R^4$ is a hydrogen atom or a lower alkyl group, $R^6$ is a group which is substituted by one or two hydroxyl groups, and $R^7$ is any of a variety of groups, including a hydroxyl group, which compounds are renin inhibitors useful as hypotensive drugs, are disclosed.

3 Claims, No Drawings

5-SUBSTITUTED AMINO-4-HYDROXY-PENTANOIC ACID DERIVATIVES AND THEIR USE

The present invention relates to 5-substituted amino-4-hydroxy-pentanoic acid derivatives useful in the pharmaceutical field. More particularly, the present invention relates to renin inhibitors expected to be useful as hypotensive drugs, a process for their production and their use as well as optically active amino alcohol derivatives useful as intermediates for the renin inhibitors and a process for their production.

A renin-angiotensin system is one of hypertensive systems in the living body, and it is an important system for regulating the blood pressure-body fluid electrolyte. Renin is secreted from renal juxtaglomerular cells and enters into the whole body circulation system via the renal vein. In the blood, there exists angiotensinogen which is a glycoprotein produced in the liver. Renin reacts on angiotensinogen to form angiotensin I. Most of angiotensin I will be converted to angiotensin II by angiotensin I-converting enzyme which is present in the pulmonary vascular cells in one cycle of pulmonary circulation. Angiotensin II thus formed directly induces contraction of smooth muscles of peripheral blood vessels and thus shows a strong hypertensive activity. It further acts on the adrenal cortex to induce secretion of aldosterone, which in turn acts on the renal to facilitate reabsorption of sodium, whereby the effective circulatory blood flow increases, the heart rate increases and the peripheral vascular resistance increases so that the blood pressure increases.

It is known that hypertension will be brought about if this renin-angiotensin system progresses abnormally. Typical examples are renal vascular hypertension and malignant hypertension. Further, as a rare case, hypertension caused by a renin producing tumor is known.

For the treatment of the hypertension due to the progress of the renin-angiotensin system, inhibitors against the angiotensin I-converting enzyme have been studied, developed and subjected to clinical tests. However, such inhibitors are suspected to have side effects, since the substrate specificity of the angiotensin I-converting enzyme is broad to some extent and there exist some enzymes similar to the angiotensin I-converting enzyme in the living body. On the other hand, it is known that renin has a strict substrate specificity. Accordingly, an inhibitor against renin has a strong specificity and can be a superior hypotensive drug. For this reason, the research on renin inhibitors has been very active, and a number of renin inhibitors have been proposed, which may be classified into the following four categories.

1. Substrate analogue peptide

This has been attempted for a long time, and the change of amino acids in the renin substrate or the conversion of the L-amino acid to the D-amino acid has been proposed (Proc. Natl. Acad. Sci. U.S.A., Vol. 77, p. 5476–5479 (1980), Biochem. Biophys. Res. Commun., Vol. 97, p. 230–235 (1980), Federation Proc., Vol. 42, p. 3155–3161 (1983), and Japanese Unexamined Patent Publication No. 10597/1986).

2. Statin or statin derivative-containing peptide

Statin is an uncommon amino acid contained in pepstatin which is a natural renin inhibitor produced by microorganisms (J. Antibiot., Vol. 23, p. 259–262 (1970), and Science, Vol. 175, p. 656 (1971)) and believed to play an important role for the development of the renin-inhibiting activity of pepstatin. A number of substrate analogue peptides of statin have been synthesized (J. Med. Chem., Vol. 23, p. 27–33 (1980), Nature, Vol. 303, p. 81–84 (1983), J. Med. Chem., Vol. 28, p. 1553–1555 (1985), J. Cardiovasc. Pharmacol., Vol. 7 (Suppl. 4), p. s58–s61 (1985), J. Med. Chem., Vol. 28, p 1779–1790 (1985), Hypertension, Vol. 8, p.II-1 to II-5 (1986), J. Med. Chem., Vol. 29, p. 2080–2087 (1986), J. Med. Chem., Vol. 29, p. 1152–1159 (1986), and Japanese Unexamined Patent Publication Nos. 89649/1984, 56194/1986, 186397/1986, 186398/1986, 29596/1987, 70349/1987, 163899/1985, 78795/1986, 152697/1986, 280459/1986, 275256/1986, 275257/1986, 275258/1986, 110661/1984, 252495/1985, 130257/1984, 90536/1983, 90539/1983, 105949/1983, 155345/1984, 34991/1985, 218398/1985, 218400/1985, 231695/1985, 243098/1985, 96/1986, 293957/1986, 100594/1986, 229851/1986 and 194097/1986).

3. Pseudo peptide having the splitting site of the substrate modified

A number of proposals have been made to modify the peptide bond at the site susceptible to hydrolysis in order to convert it to a bonding mode which is hardly susceptible to the hydrolysis and which is as close as possible to the peptide bond.

(1) Hydroxyethylene type (Hypertension, Vol. 3, p.13–18 (1985), Hypertension, Vol. 8, p. 1105–1112 (1986) and Japanese Unexamined Patent Publication Nos. 63641/1986, 136594/1985, 122296/1986, 53952/1987, 59846/1982, 50415/1985 and No. 293957/1986)

(2) Methylene amino type (carbonyl reduction type) (Nature, Vol. 299, p. 555–557 (1982), Biochem. Biophys. Res. Commun., Vol. 139, p. 982–990 (1986), and Japanese Unexamined Patent Publication Nos. 500415/1985 and 59846/1982)

(3) Phosphinicomethylene type (Japanese Unexamined Patent Publication Nos. 33197/1987 and 26288/1987)

(4) Olefin type (J. Med. Chem., Vol. 27, p. 1351–1354 (1984))

(5) Retro-inverso amide type (Japanese Unexamined Patent Publication Nos. 231055/1984 and 231056/1984)

4. Others

Various inhibitors have been prepared by modifying those belonging to the above category 3.

(1) Aldehyde type (Biochem. Biophys. Res. Commun., Vol. 118, p. 929–933 (1984), Hypertension, Vol. 7 (Suppl. I), p. I-8 to I-11 (1985), FEBS Lett., Vol. 167, p. 273–276 (1984), Japanese Unexamined Patent Publication Nos. 100595/1986, 137896/1986, 148167/1986 and 227851/1984 and Japanese Examined Patent Publication No. 39149/1983)

(2) Glycol or thioglycol type (Biochem. Biophys. Res. Commun., Vol. 132, p. 155–161 (1985), Biochem. Biophys. Res. Commun., Vol. 143, p. 44–51 (1987), and Japanese Unexamined Patent Publication Nos. 33152/1986, 200970/1986, 33141/1987 and 263998/1986)

(5 3) Norstatin type (J. Med. Chem., Vol. 25, p. 605–610 (1982), Europ. J. Pharmacol., Vol. 129, p. 393–396 (1986) and Japanese Unexamined Patent Publication Nos. 176573/1986, 186366/1986, 236770/1986, 4286/1987, 33156/1987, 56458/1987 and 163899/1985)

(4) Hydroxyethyleneamino type (Biochem. Biophys. Res. Commun., Vol. 134, p. 71–77 (1986) and Japanese Unexamined Patent Publication Nos. 200970/1986, 118352/1986, 137897/1986, 136595/1985 and 33141/1987)

Among the above publications, Japanese Unexamined PCT Publication No. 500415/1985 and Japanese Unexamined Patent Publication No. 122296/1986 disclose compounds having a homostatin structure represented by the following formula:

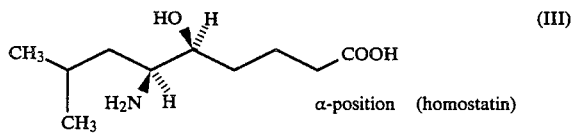

Japanese Unexamined PCT Publication No. 500415/1985 discloses as a substituent at the α-position of homostatin a group of the formula —$(CH_2)_m$—$NH_2$ or —$(CH_2)_m$—OH wherein m is 2, 3 or 4. On the other hand, Japanese Unexamined Patent Publication No. 122296/1986 discloses as a substituent at the α-position of homostatin a lower alkyl group having at least two carbon atoms, a hydroxy-lower alkyl group which may be esterified or etherified, a cycloalkyl group, a cycloalkyl-lower alkyl group, a bicycloalkyl group, a bicycloalkyl-lower alkyl group, a tricycloalkyl group, a tricycloalkyl-lower alkyl group, an aryl group, an aryl-lower alkyl group, a carbamoyl group which may be substituted, a hydroxyl group which may be substituted or a mercapto group which may be substituted. However, both publications are based on the concept of the pseudo peptide having a splitting site of the substrate modified, and a substrate analogue amino acid side chain is sought as the substituent. Accordingly, there is no specific disclosure with respect to a lower alkyl group substituted by a hydroxyl group or a substituent substituted by a hydroxyl group. Likewise, there is no teaching or suggestion that excellent renin inhibiting activities can be obtained by the substitution with a hydroxyl group.

On the other hand, for the production of a statin derivative, it is known to obtain an optically highly pure statin derivative by the optical resolution of a mixture of diastereomers obtained by extending the carbon chain of a L-leucine as the starting material (Journal of Organic Chemistry, Vol. 43, p. 3624–3626 (1978), Japanese Unexamined Patent Publication No. 130257/1984 and Japanese Unexamined PCT Publication No. 500415/1985). However, such optical resolution is not advantageous from the industrial point of view.

It is therefore an object of the present invention to produce statin derivatives without using optical resolution, and to provide compounds which have excellent renin inhibiting activities and which are thus expected to be useful as hypotensive drugs.

The present inventors have paid attention to the statin moiety which plays an important role for the development of the renin inhibiting activity of pepstatin and have synthesized various statin derivatives and studied the renin inhibiting activities of such derivatives. As a result, it has been found that a group of compounds represented by the formula I given hereinafter, wherein a substituent having one or two hydroxyl groups is introduced to the carbon atom at the α-position of homostatin as an analogue of statin, exhibit excellent renin inhibiting activities. Further, it has been found possible to produce statin derivatives with stereospecificity by using pepstatin as the starting material. In addition, novel amino alcohol derivatives represented by the formulas III and IV given hereinafter have been found useful as intermediates for the production of the compounds expected to be useful as renin inhibitors. The present invention has been accomplished on the basis of these discoveries.

The present invention provides a 5-substituted amino-4-hydroxy-pentanoic acid derivative having the formula:

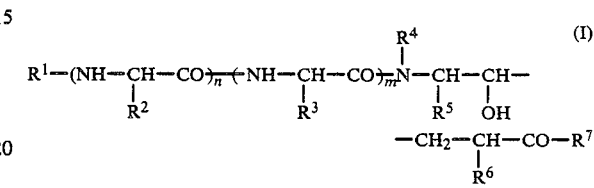

wherein $R^1$ is a hydrogen atom, a lower alkoxycarbonyl group, an aryloxycarbonyl group, an aralkyloxycarbonyl group or a lower alkanoyl group which may be substituted by from one to three substituents selected from the group consisting of an amino group, a hydroxyl group, a carboxyl group, an aryloxy group, an aralkyloxycarbonylamino group, a lower alkoxycarbonylamino group and a

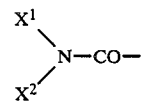

group wherein each of $X^1$ and $X^2$ which may be the same or different is a hydrogen atom, a lower alkyl group, an aryl group or an aralkyl group, or $X^1$ and $X^2$ form together with the adjacent nitrogen atom a 5- or 6-membered heterocyclic group which may further contain a hetero atom selected from the group consisting of a nitrogen atom, an oxygen atom and a sulfur atom and which may further contain a double bond in its carbon chain, each of $R^2$, $R^3$ and $R^5$ which may be the same or different is a hydrogen atom, a lower alkyl group or a residue of an acidic, neutral or basic amino acid, $R^4$ is a hydrogen atom or a lower alkyl group, $R^6$ is a lower alkyl, cycloalkyl, cycloalkylalkyl or aralkyl group which is substituted by one or two hydroxyl groups, $R^7$ is a hydroxyl group, a —OY group wherein Y is a lower alkyl group, an aryl group, an aralkyl group, a lower alkoxyalkyl group, a lower alkanoyloxyalkyl group, a lower alkoxycarbonyloxyalkyl group or a 1-phthalidyl group, or a

group wherein each of $Y^1$ and $Y^2$ which may be the same or different is a hydrogen atom, a lower alkyl group, an aryl group, an aralkyl group or a cycloalkyl group, or $Y^1$ and $Y^2$ form together with the adjacent nitrogen atom a 5- or 6-membered heterocyclic group which may further contain a hetero atom selected from the group consisting of a nitrogen atom, an oxygen atom and a sulfur atom, and each of n and m which may be the same or different is 0 or 1.

According to the present invention, the pentanoic acid derivative of the formula I can be produced by a process which comprises reducing in an inert solvent a 5-substituted amino-4-hydroxy-pentenoic acid having the formula:

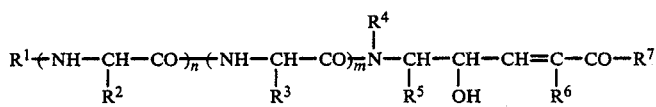 (II)

wherein m, n, $R^1$, $R^2$, $R^3$, $R^4$, $R^5$, $R^6$ and $R^7$ are as defined above.

The present invention also provides a hypotensive drug which comprises an effective amount of the pentanoic acid derivative of the formula I and a pharmaceutically acceptable carrier.

Further, the present invention provides an optically active substituted amino alcohol derivative having the formula:

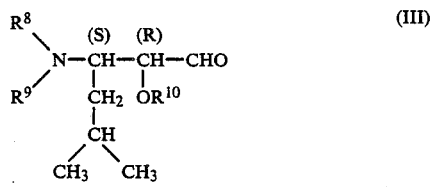 (III)

wherein each of $R^8$ and $R^9$ which may be the same or different is a hydrogen atom, an acyl group or an amino-protecting group, $R^{10}$ is a hydrogen atom or a hydroxyl-protecting group, or $R^8$ and $R^9$ together form a bivalent amino-protecting group, or $R^9$ and $R^{10}$ together form a carbonyl group or a

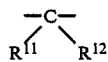

group wherein each of $R^{11}$ and $R^{12}$ which may be the same or different is a hydrogen atom, a lower alkyl group or an aryl group which may be substituted, or $R^{11}$ and $R^{12}$ together form a lower alkylene group, provided that when $R^9$ and $R^{10}$ together form the

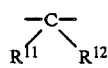

group, either $R^{11}$ or $R^{12}$ and $R^8$ may together form a single bond, and another optically active substituted amino alcohol derivative having the formula:

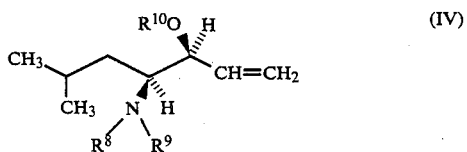 (IV)

wherein $R^8$, $R^9$ and $R^{10}$ are as defined above.

Furthermore, the present invention provides processes for the production of the optically active substituted amino alcohol derivatives of formulas III and IV.

Now, the present invention will be described in detail with reference to the preferred embodiments.

Firstly, the definitions of various terms referred to in this specification and some specific examples falling within such terms will be given.

The lower alkyl group may be a straight chain or branched alkyl group having from 1 to 6 carbon atoms such as a methyl group, an ethyl group, a propyl group, an isopropyl group, a butyl group, an isobutyl group, a sec-butyl group, a tert-butyl group, a pentyl group or a hexyl group.

The aryl group may be an aryl group having from 6 to 10 carbon atoms such as a phenyl group, a 3-methylphenyl group, a 4-methylphenyl group, a 4-ethylphenyl group, a 4-propylphenyl group, a 2-hydroxyphenyl group, a 4-methoxyphenyl group, a 2,4-dimethoxyphenyl group, a 4-dimethylaminophenyl group, a 2-nitrophenyl group, a 1-naphthyl group or a 2-naphthyl group.

The aralkyl group may be an aralkyl group having from 7 to 10 carbon atoms such as a benzyl group, a (1-naphthyl)methyl group, a (2-naphthyl)methyl group, a phenethyl group, a 3-phenylpropyl group, a 2-methyl-2-phenylpropyl group or a 4-phenylbutyl group.

The cycloalkyl group may be a cycloalkyl group having from 3 to 6 carbon atoms such as a cyclopropyl group, a cyclobutyl group, a cyclopentyl group or a cyclohexyl group.

The lower alkoxycarbonylamino group may be a lower alkoxycarbonylamino group having from 2 to 7 carbon atoms such as a methoxycarbonylamino group, an ethoxycarbonylamino group, a propoxycarbonylamino group, an isopropoxycarbonylamino group, a butoxycarbonylamino group, an isobutoxycarbonylamino group, a tert-butoxycarbonylamino group, a pentyloxycarbonylamino group or a hexyloxycarbonylamino group.

The aryloxycarbonyl group may be an aryloxycarbonyl group having from 7 to 11 carbon atoms such as a phenoxycarbonyl group, a 4-methylphenyloxycarbonyl group, a 4-ethylphenyloxycarbonyl group, a 4-isopropylphenyloxycarbonyl group, a 4-tert-butylphenyloxycarbonyl group, a (1-naphthyl)oxycarbonyl group or a (2-naphthyl)oxycarbonyl group.

The aryloxy group may be an aryloxy group having from 6 to 10 carbon atoms such as a phenoxy group, a 4-methylphenyloxy group, a 4-ethylphenyloxy group, a 4-isopropylphenyloxy group, a (1-naphthyl)oxy group or a (2-naphthyl)oxy group.

The aralkyloxycarbonyl group may be an aralkyloxycarbonyl group having from 8 to 12 carbon atoms such as a benzyloxycarbonyl group, a phenethyloxycarbonyl group, a 3-phenylpropyloxycarbonyl group, a 4-phenylbutyloxycarbonylgroup, a (1-naphthyl)methyloxycarbonyl group or a (2-naphthyl)methyloxycarbonyl group.

The aralkyloxycarbonylamino group may be an aralkyloxycarbonylamino group having from 7 to 12 carbon atoms such as a benzyloxycarbonylamino group, a phenethyloxycarbonylamino group, a 3-phenylpropyloxycarbonylamino group, a 4-phenylbutyloxycarbonylamino group, a (1-naphthyl)methyloxycarbonylamino group or a (2-naphthyl)methyloxycarbonylamino group.

The lower alkoxycarbonyl group may be a lower alkoxycarbonyl group having from 2 to 7 carbon atoms such as a methoxycarbonyl group, an ethoxycarbonyl group, a propoxycarbonyl group, an isopropoxycarbonyl group, a butoxycarbonyl group, a sec-butoxycarbonyl group, a tert-butoxycarbonyl group, a pentyloxycarbonyl group or a hexyloxycarbonyl group.

The lower alkoxyalkyl group may be a lower alkoxyalkyl group having from 2 to 7 carbon atoms such as a methoxymethyl group, an ethoxymethyl group, a 1-methoxyethyl group, 2-methoxyethyl group, a 1-ethoxyethyl group, a 2-ethoxyethyl group, a propoxymethyl group, an isopropoxymethyl group, a butoxymethyl group, an isobutoxymethyl group or a hexyloxymethyl group.

The lower alkanoyloxyalkyl group may be a lower alkanoyloxyalkyl group having from 3 to 7 carbon atoms such as an acetoxymethyl group, a propionyloxymethyl group, a butylyloxymethyl group, an isobutylyoxymethyl group, a valeryloxymethyl group, a pivaloyloxymethyl group, a 1-acetoxyethyl group, a 2-acetoxyethyl group, a 1-butylyloxyethyl group, a 2-butylyloxyethyl group, a 1-pivaloyloxyethyl group or a 2-pivaloyloxyethyl group.

The lower alkoxycarbonyloxyalkyl group may be a lower alkyloxycarbonylalkyl group having from 3 to 9 carbon atoms such as a methoxycarbonyloxymethyl group, an ethoxycarbonyloxymethyl group, a propoxycarbonyloxymethyl group, an isopropoxycarbonyloxymethyl group, a butoxycarbonyloxymethyl group, a tert-butoxycarbonyloxymethyl group, a 1-methoxycarbonyloxyethyl group, 2-methoxycarbonyloxyethyl group, a 1-ethoxycarbonyloxyethyl group, a 2-ethoxycabonyloxyethyl group, a 1-tert-butoxycarbonyloxyethyl group, a 2-tert-butoxycarbonyloxyethyl group, a 1-butoxycarbonyloxyethyl group, a 1-pentyloxycarbonyloxyethyl group or a 1-hexyloxycarbonyloxyethyl group.

In the

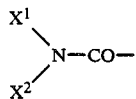

group wherein $X^1$ and $X^2$ are as defined above and the

group wherein $Y^1$ and $Y^2$ are as defined above, when $X^1$ and $X^2$ or $Y^1$ and $Y^2$ form together with the above, when X- and X adjacent nitrogen atom a 5- or 6-membered heterocyclic group which may further contain a hetero atom selected from the group consisting of a nitrogen atom, an oxygen atom and a sulfur atom, such a 5- or 6-membered heterocyclic group may be a morpholino group, thiomorpholino group, a pyrrolidinyl group or a piperazinyl group.

The residue of an acidic, neutral or basic amino acid may be a residue of an amino acid such as alanine, arginine, histidine, homoserine, leucine, naphthylalanine, norleucine, lysine, norvaline, ornithine, serine, threonine, tyrosine, valine, aspartic acid, glutamic acid, tryptophan, isoleucine, phenylalanine or cysteine.

The lower alkanoyl group which may be substituted by one to three substituents selected from the group consisting of an amino group, a hydroxyl group, a carboxyl group, an aryloxy group, an aralkyloxycarbonylamino group, a lower alkoxycarbonylamino group or a group wherein $X^1$ and $X^2$ are as defined above and which may further contain a double bond in the carbon chain, may be a lower alkanoyl group which may be substituted, such as an acetyl group, a propionyl group, a butyryl group, an isobutyryl group, a valeryl group, an isovaleryl group, a hexanoyl group, a phenoxyacetyl group, a (1-naphthyl)oxyacetyl group, a cinnamoyl group, a (2-naphthyl)oxyacetyl group, a 3-phenylpropanoyl group, a 3-phenyl-2-hydroxypropanoyl group, a 3-phenyl-2-phenylpropanoyl group, a 3-phenyl-2-benzylpropanoyl group, a 4-phenyl-2-benzylbutyryl group, a 5-phenyl-2-benzylpentanoyl group, a 2-benzyl-4-phenyl-3-butenoyl group, a 4-benzyloxycarbonylaminobutyryl group, a 3-methoxycarbonyl-2,3-dihydroxypropionyl group, a 3-morpholinocarbonyl-2-[(1-naphthyl)methyl]-propanoyl group, a 3-morpholinocarbonyl-2-[(2-naphthyl)methyl]-propanoyl group or a 4-aminobutyryl group.

The lower alkyl, cycloalkyl, cycloalkylalkyl or aralkyl group which is substituted by one or two hydroxyl groups includes a hydroxymethyl group, a 2-hydroxyethyl group, a 3-hydroxypropyl group, a 4-hydroxybutyl group, a 5-hydroxypentyl group, a 2,3-dihydroxypropyl group, a 3,4-dihydroxybutyl group a 4,5-dihydroxypentyl group, a 1-hydroxyethyl group, a 1-hydroxypropyl group, a 1-hydroxybutyl group, a 1-hydroxypentyl group, a 2-hydroxy-1-hydroxymethylethyl group, a 3-hydroxy-2-hydroxymethylpropyl group, a 4-hydroxy-3-hydroxymethylbutyl group, a '-hydroxy-2,2-dihydroxymethylpropyl group, a 4-hydroxy-2,3-dihydroxylmethylbutyl group, a 2-hydroxymethyl-2,3-dihydroxypropyl group, a 2-hydroxymethylbutyl group, a 4-hydroxymethylbutyl group, a 3-hydroxy-3-cyclohexylpropyl group, 4-hydroxy-4-cyclohexylbutyl group, a 3-hydroxy-3-cyclopentylpropyl group, a 4-hydroxy-4-cyclopentylbutyl group, a 4-hydroxybenzyl group, a 3-hydroxybenzyl group, a 2-hydroxybenzyl group, a 4-hydroxyphenethyl group, a 3-hydroxyphenethyl group, a 2-hydroxyphenethyl group, an α-hydroxybenzyl group, a 2-phenyl-2-hydroxyethyl group, a 2-phenyl-1-hydroxyethyl group and a 3-phenyl-3-hydroxypropyl group.

The lower alkylene group may be a lower alkylene group having from 4 to 6 carbon atoms such as a tetramethylene group, a pentamethylene group or a hexamethylene group.

The acyl group may be a lower alkanoyl group such as a formyl group, an acetyl group, a propionyl group, a butyryl group, an isobutyryl group, a valeryl group, or an isovaleryl group, an aroyl group such as a benzoyl group, or an acyl group derived from the carboxyl group of an amino acid, a di- or penta-peptide or a derivative thereof, such as an N-benzyloxycarbonyl-naphthylalanylhistidyl group, an N-tert-butoxycarbonylnaphthylalanylhistidyl group, an N-benzyloxycarbonylnaphthylalanylnorleucyl group, an N-tert-butoxycarbonylnaphthylalanylnorleucyl group, an N-tert-butoxycarbonylphenylalanylhistidyl group, an N-benzyloxycarbonylphenylalanylhistidyl group, an N-tert-butoxycarbonylphenylalanylnorleucyl group, an N-benzyloxycarbonylphenylalanylnorleucyl group, an N-isovalerylnaphthylalanylhistidyl group, an N-isovalerylnaphthylalanylnorleucyl group, an N-isovalerylphenylalanylnorleucyl group, an N-isovalerylphenylalanylhistidyl group, an N-[2-(1-naphthyl)methyl-4-oxo-4-morpholinobutyryl]norleucyl group, an N-acetylphenylalanylhistidyl group, an N-[2-(1-naphthyl)methyl-4-oxo-4-morpholinobutyryl]histidyl group, an N-isovalerylhistidylprolylphenylalanylhistidyl group, an N-(2-benzyl-3-phenylpropionyl)histidyl group, an N-(2,3-diphenylpropionyl)histidyl group, an N-(2-benzyl-4-phenylbutyryl)histidyl group, an N-(2-benzyl-5-phenylvaleryl)histidyl group, an N-(2-benzyl-6-phenylhexanoyl)histidyl group, an N-(2-benzyl-3-phenylpropionyl)norleucyl group, an N-(2,3-diphenylpropionyl)norleucyl group, an N-(2-benzyl-4-phenylbutyryl)norleucyl group, an N-(2-benzyl-5-valeryl)norleucyl group, an N-(2-benzyl-6-phenylhexanoyl)norleucyl group, an N-(2-styryl-3-phenylpropionyl)histidyl group, an N-(2-styryl-3-phenylpropionyl)norleucyl group, an N-phenoxyacetylhistidyl group, an N-phenoxyacetylnorleucyl group, an N-(3-phenylpropionyl)histidyl group, an N-(3-phenylpropionyl)norleucyl group, an arginylarginylprolylphenylalanylhistidyl group, an N-benzyloxycarbonylarginylarginylprolylphenylalanylhistidyl group, an N-benzyloxycarbonylarginylprolylphenylalanylhistidyl group, a prolylhistidylprolylphenylalanylhistidyl group, an N-isovalerylphenylalanylnorvaleryl group, an N-tert-butoxycarbonylphenylalanylphenylalanyl group, a histidylprolylphenylalanylhistidyl group, a histidylprolylphenylalanylnorleucyl group, an N-(2-hydroxy-3-phenylpropionyl)histidyl group, an N-(2-hydroxy-3-phenylpropionyl)norleucyl group, an N-tert-butoxycarbonylphenylalanyl-N-methylhistidyl group, an N-(2,3-dihydroxy-3-methoxycarbonylpropionyl)phenylalanylhistidyl group, an N-(4-benzyloxycarbonylaminobutyryl)glycylphenylalanylhistidyl group, or an N-(4-aminobutyryl)glycylphenylalanylhistidyl group.

The amino-protecting group may be a known amino-protecting group such as a benzyloxycarbonyl group, a p-methoxybenzyloxycarbonyl group, a tert-butoxycarbonyl group, a chloroacetyl group, a p-toluenesulfonyl group, a benzyl group, a 3,4-dimethoxybenzyl group, an o-nitrobenzyl group, a p-methoxybenzyl group, a furfuryloxycarbonyl group, a p-nitrobenzyloxycarbonyl group, a (2-chloro-1-inden-1-yl)oxycarbonyl group, a 4-methoxy-2,3,6-trimethylbenzenesulfonyl group, a diphenylphosphinothioyl group, a trityl group, a vinyloxycarbonyl group, an 9-anthrylmethyloxycarbonyl group, a cyclobutoxycarbonyl group, a 1-methylcyclobutoxycarbonyl group, a cyclopropylmethoxycarbonyl group, a diphenylphosphinyl group, a dimethylphosphinothioyl group, an o-nitrophenylsulfenyl group, a dithiasuccinoyl group, a 1-cyclopropylethyloxycarbonyl group, a diphenylmethyloxycarbonyl group or a trifluoroacetyl group.

The bivalent amino-protecting group may be a known bivalent amino-protecting group such as a phthaloyl group.

The hydroxyl-protecting group may be a known hydroxyl-protecting group such as a 2-methoxyethoxymethyl group, a 2-methoxyethyl group, a methoxymethyl group, a tetrahydropyranyl group, a 2-methoxytetrahydrofuranyl group, a 2-methoxytetrahydropyranyl group, a trimethylsilyl group, a tert-butyldimethylsilyl group, an acetyl group, a chloroacetyl group, a benzoyl group, a benzyl group or a p-methoxybenzyl group.

In a case where $R^9$ and $R^{10}$ together form a carbonyl group or a

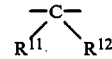

group wherein each of $R^{11}$ and $R^{12}$ which may be the same or different is a hydrogen atom, a lower alkyl group or an aryl group which may be substituted, or $R^{11}$ and $R^{12}$ may together form a lower alkylene group or in case where when $R^9$ and $R^{10}$ together form the

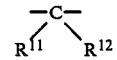

group, either $R^{11}$ or $R^{12}$ and $R^8$ together form a single bond, such a protecting group may be a known bivalent protecting group used for simultaneously protecting an amino group and a hydroxyl group present in the same molecule in the adjacent position to each other, such as:

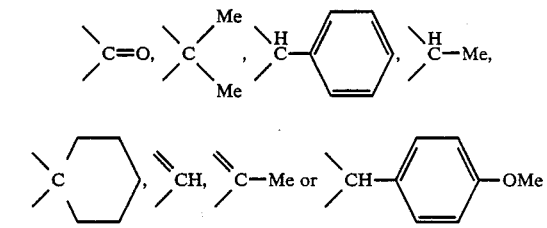

In the compound of the formula I of the present invention, the carbon atoms substituted by $R^5$, the hydroxyl group and $R^6$ may have R-configuration, S-configuration or RS-configuration.

When the compound of the present invention is in the form of a salt, such a salt may be any pharmaceutically acceptable non-toxic salt. For example, it may be a salt with an inorganic acid such as hydrochloric acid, sulfuric acid, hydrobromic acid or phosphoric acid, or a salt with an organic acid such as oxalic acid, maleic acid, acetic acid, formic acid or tartaric acid. Now, the process for the preparation of the compound of the present invention will be described.

The compound of the formula I of the present invention can be produced by a process which will be described below.

A corresponding L-amino acid may usually be employed as the starting material. Firstly, the amino group of the amino acid is protected by a usual amino-protecting group e.g. an alkyloxycarbonyl or aralkyloxycarbonyl group such as a benzyloxycarbonyl group, a 4-methoxybenzyloxycarbonyl group or a tert-butyloxycarbonyl group, a diacyl group such as a phtharyl group, an acyl group such as a trifluoroacetyl group or a dichloroacetyl group, or an aralkyl group such as a benzyl group or a trityl group, then the carboxylic acid is preferably converted to an amide, an ester, an acid halide or an acid anhydride, and then the material is reduced by a conventional method such as Birch reduction, catalytic reduction or reduction by means of a metal hydride complex compound to form an aldehyde having the formula:

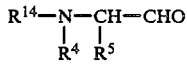  (X)

wherein $R^{14}$ is an amino-protecting group, and $R^4$ and $R^5$ are as defined above. A suitable method is selected depending upon the type of the amino group or the protecting group on the amino acid side chain. For instance, in the case of L-benzyloxycarbonylleucine, it is converted to pyrazolide by means of a condensation agent such as dicyclohexylcarbodiimide and pyrazole followed by the reduction with a metal hydride compound such as lithium aluminum hydride to obtain L-benzyloxycarbonylleucinal.

The aldehyde of the formula X is treated with a cyanide such as sodium cyanide or potassium cyanide, if necessary after converting it into an adduct with acid sodium sulfite, to obtain cyanohydrin, and then the nitrile group is hydrolyzed with an acid or base to obtain a compound having the formula:

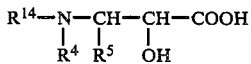  (XI)

wherein $R^4$, $R^5$ and $R^{14}$ are as defined above. The compound of the formula XI is obtainable in the form of a mixture of diasteroisomers, which may be separated by a usual separating means such as column chromatography or a high speed liquid chromatography. One of such specific methods for the synthesis is described in detail in Agricultural Biological Chemistry, Vol. 46, p. 1865–1872 (1982).

If necessary, the hydroxyl group of the compound XI may be protected by a usual hydroxyl-protecting group such as a 2-methoxyethoxymethyl group, a 2-methoxyethyl group, a methoxymethyl group, a tetrahydropyranyl group, a 2-methoxytetrahydrofuranyl group, a 2-methoxytetrahydropyranyl group, a trimethylsilyl group, a tert-butyldimethylsilyl group, an acetyl group, a chloroacetyl group, a benzoyl group, a benzyl group or a 4-methoxybenzyl group, and then, the carboxylic acid of the compound of the formula XI is converted to a carboxylic acid amide, a carboxylic acid ester, an acid halide or an acid anhydride by the above-mentioned method, i.e. by a conventional method. Then, the compound is reduced by a conventional method such as Birch reduction, catalytic reduction or a reduction by means of a metal hydride complex compound, whereby when a compound of the formula XI having R-configuration at the α-position is employed, it is possible to obtain a compound having the formula:

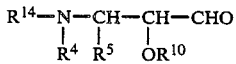  (III')

wherein $R^{10}$ is a hydrogen atom or a hydroxyl-protecting group, and $R^4$, $R^5$ and $R^{14}$ are as defined above.

Referring to the second aspect of the present invention, the compounds of the formulas III and IV can be produced as follows.

Namely, pepstatin is hydrolyzed to obtain of statin having the formula:

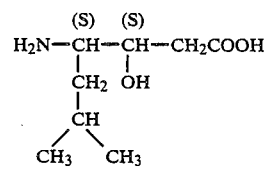  (V)

Then, optional substituents are introduced to the functional groups of statin of the formula V to obtain a compound having the formula:

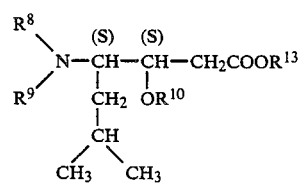  (VI)

wherein $R^{13}$ ia lower alkyl group, each of $R^8$ and $R^9$ which may be the same or different is a hydrogen atom, an acyl group or an amino-protecting group, $R^{10}$ is a hydrogen atom or a hydroxyl-protecting group, or $R^8$ and $R^9$ together form a bivalent amino protecting group, or $R^9$ and $R^{10}$ together form a carbonyl group or a

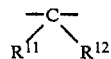

group wherein each of $R^{11}$ and $R^{12}$ which may be the same or different is a hydrogen atom, a lower alkyl group or an aryl group which may be substituted, or $R^{11}$ and $R^{12}$ together form a lower alkylene group, provided that when $R^9$ and $R^{10}$ form the

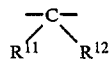

group, either $R^{11}$ or $R^{12}$ and $R^8$ may together form a single bond. Then, the compound of the formula VI is converted to a compound having the formula:

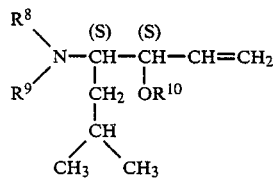  (IV)

wherein $R^8$, $R^9$ and $R^{10}$ are as defined above. Then, the compound of the formula IV can be converted to a compound having the formula:

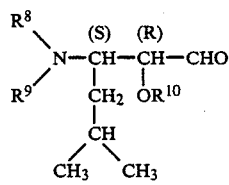
(III)

wherein $R^8$, $R^9$ and $R^{10}$ are as defined above.

Pepstatin, the starting material of the present invention, can be readily prepared by a known method such as a method disclosed in Journal of Antibiotics, Vol. 23, p. 259–262 (1970) wherein a pepstatin-producing microorganism is cultured, and pepstatin is isolated from the culture medium.

The step of hydrolyzing pestatin to obtain statin of the formula V is conducted under a reaction condition usually employed for the hydrolysis of a peptide. As such a reaction condition, it is preferred to conduct the reaction, for example, in a concentrated hydrochloric acid at a temperature of from 30° to 40° C. for two days, or in a concentrated hydrochloric acid at room temperature for 1 to 2 weeks, or in a 6N hydrochloric acid under heating and refluxing for from 18 to 28 hours. The isolation of statin of the formula V from the reaction solution obtained by the hydrolysis, may be conducted by a purification method which is commonly used for the purification of an amino acid. Preferably, the isolation can be conducted by a purification method by means of a cation exchange resin such as Dowex 50®.

The step of introducing optional substituents to the functional groups of statin of the formula V to obtain a compound of the formula VI, may be conducted by a method known per se. The protection of the amino group and the hydroxyl group may be conducted in accordance with the method disclosed in Organic Synthetic Chemistry, Vol. 36, p. 740–748 (1978), Bulletin of the Chemical Society of Japan, Vol. 46, p. 3308–3310 (1973) and Journal of Medicinal Chemistry, Vol. 23, p. 27–33 (1980). The introduction of an acyl group into an amino group may be conducted by reacting the amino group with a carboxylic acid derived from the acyl group or its reactive derivative by any conventional peptide synthesis such as a dicyclohexylcarbodiimide method, a mixed acid anhydride method, an azide method, an active ester method or an acid halide method. The conversion of the carboxyl group to a lower alkyl ester may be conducted by a conventional esterification method which does not adversely affect other substituents, for example, by reacting it with a lower alkanol such as methanol or ethanol in the presence of an acid catalyst such as hydrochloric acid, hydrobromic acid or p-toluenesulfonic acid, or by reacting it with diazomethane in the case methyl esterification. In this step, the order of introduction of various substituents to the functional groups may be changed as the case requires.

The step of converting the compound of the formula VI to a compound of the formula IV may be conducted, for example, by a process which comprises reducing the compound of the formula VI to obtain a compound having the formula:

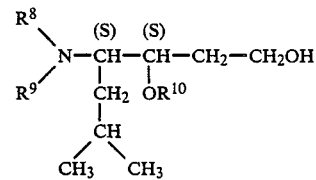
(VII)

$R^8$, $R^9$ and $R^{10}$ are as defined above, then converting the compound of the formula VII to a compound having the formula:

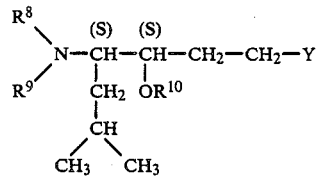
(VIII)

wherein Y is a leaving group, $R^8$, $R^9$ and $R^{10}$ are as defined above, then halogenating the compound of the formula VIII to obtain a compound having the formula:

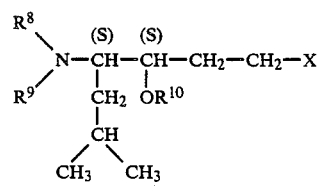
(IX)

wherein X is a halogen atom, and $R^8$, $R^9$ and $R^{10}$ are as defined above, and then treating the compound of the formula IX with a base to obtain the compound of the formula IV. Here, the halogen atom may be, for example, a chlorine atom or a bromine atom, and the leaving group may be, for example, an acetoxy group, a p-toluenesulfonyloxy group or a methanesulfonyloxy group.

The step of converting the compound of the formula VI to the compound of the formula VII may be conducted by any conventional method so long as it is capable of reducing the carboxylate group of the compound of the formula VI to an alcohol. Preferably, a method may be mentioned wherein the compound of the formula VI is reduced in a solvent such as methanol, ethanol, tetrahydrofuran, dimethylformamide or dimethylacetamide by means of a metal hydride complex compound such as sodium borohydride or lithium borohydride.

The step of converting the compound of the formula VII to the compound of the formula VIII may be conducted by reacting the compound of the formula VII with p-toluenesulfonylchloride, methanesulfonylchloride or acetylchloride in the presence of a base such as pyridine or triethylamine.

The step of converting the compound of the formula VIII to the compound of the formula IX may be conducted by reacting the compound of the formula VIII with a halogen donating agent such as lithium chloride or lithium bromide in a solvent such as dimethylformamide, dimethylacetamide, tetrahydrofuran or acetonitrile.

The step of converting the compound of the formula IX to the compound of the formula IV may be conducted by treating the compound of the formula IX with an organic amine such as triethylamine or 1,8-diazabicyclo[5,4,0]-7-undecene, an alkali metal or alkaline earth metal hydroxide such as sodium hydroxide, potassium hydroxide or barium hydroxide, or a metal alcoholate such as sodium methoxide, potassium methoxide or potassium tert-butoxide.

The step of converting the compound of the formula IV to the compound of the formula III may be conducted by treating the compound of the formula IV with an oxidizing agent such as chromic acid, a periodate, osmium tetraoxide, ozone or a combination of these reagents. A compound of the formula III wherein $R^5$ is an isobutyl group can be produced stereospecifically.

The compound of the formula III or III' is reacted with a compound having the formula:

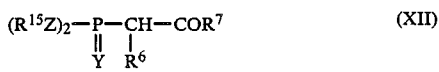
(XII)

wherein Y is an oxygen atom or a sulfur atom, Z is nil, an oxygen atom or a nitrogen atom, $R^{15}$ is a lower alkyl group or an aryl group, and $R^6$ and $R^7$ are as defined above, or the formula:

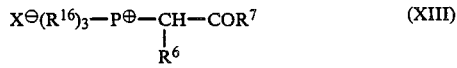
(XIII)

wherein X is a halogen atom, $R^{16}$ is an aryl group, and $R^6$ and $R^7$ are as defined above, preferably in a stream of an inert gas such as argon or nitrogen, in a solvent not adversely affecting the reaction, such as tetrahydrofuran or dimethylformamide, if necessary by an addition of a halide of an alkali metal or an alkaline earth metal, such as lithium chloride, lithium bromide or magnesium bromide, and further by an addition of a base e.g. a tertiary amine such as diazabicyloundecene, triethylamine or diisopropylethylamine, or a hydride, hydroxide, alcoholate or alkylated product of an alkali metal such as sodium hydride, sodium hydroxide, sodium ethoxide or butyl lithium, to obtain a compound having the formula:

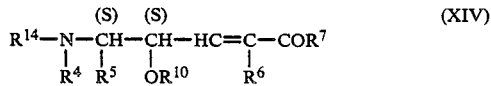
(XIV)

wherein $R^4$, $R^5$, $R^6$, $R^7$, $R^{10}$ and $R^{14}$ are as defined above. When $R^4$ is a lower alkyl group, the preferred stage for its introduction differs depending upon the particular alkylation method. For example, although the production according to this process may be carried out by using an N-alkylamino acid as the starting material, it is preferred to introduce a lower alkyl group, for instance, by reacting an alkyl halide such as methyliodide or ethyliodide to the compound of the formula XV in the presence of a base such as triethylamine.

Then, the compound of the formula XIV can be catalytically reduced in the presence of a metal catalyst such as palladium black, palladium-carbon or platinum oxide to obtain a compound having the formula:

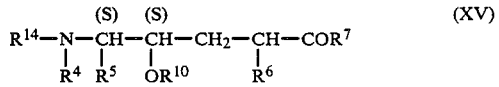
(XV)

wherein $R^4$, $R^5$, $R^6$, $R^7$, $R^{10}$ and $R^{14}$ are as defined above. The protecting groups $R^{10}$ and $R^{14}$ may be simultaneously removed by this reaction, if they are protecting groups which can be removed by the catalytic reduction. However, the protecting groups $R^{10}$ and $R^{14}$ are usually removed by a conventional method suitable for the removal of such protecting groups to obtain a compound having the formula:

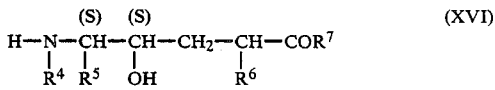
(XVI)

wherein $R^4$, $R^5$, $R^6$ and $R^7$ are as defined above.

The compound of the formula XVI is reacted with a compound having the formula:

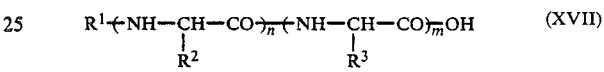
(XVII)

wherein $R^1$, $R^2$, $R^3$, n and m are as defined above, by a usual method for the peptide synthesis, such as an azide method, an activated ester method, a mixed acid anhydride method, a carbodiimide method, an imidazole method, a diphenylphosphorylazide method, a woodword method or a condensation method in an oxidation-reduction system, to obtain a compound of the formula I of the present invention.

The order for linking such constituting components may not necessarily follow the above sequence and may suitably be selected depending upon the particular compound to be produced.

When the compound of the present invention is to be used as a medicine, it may be administered by itself, but it is usually administered as a mixture with a carrier suitably selected depending upon the route for administration and standard formulations. For example, for oral administration, the, compound of the present invention may be administered in the form of tablets which may be prepared by adding to a powder of the active ingredient of the present invention an excipient such as starch, lactose, sucrose, glucose, crystalline cellulose, calcium carbonate or kaolin, a binder such as a starch solution, a gelatin solution, a hydroxypropyl cellulose, a glucose solution, a sucrose solution, water or ethanol, a disintegrator such as starch, agar, gelatin powder, CMC-Ca, CMC-Na, crystalline cellulose, calcium carbonate or sodium hydrogencarbonate, or a lubricant such as magnesium stearate, calcium stearate, talc, macrogoal 4,000, macrogoal 6,000 or stearic acid, subjecting the mixture to compression molding by a conventional tabletting method, and if necessary, applying a sugar coating by means of a concentrated sugar solution containing e.g. gum arabic, talc, polyvinyl pyrrolidone, polyethylene glycol and/or titanium oxide, applying a film coating by means of a film-forming agent composed of e.g. polyvinyl acetal, diethylaminoacetate, cellulose acetate, N,N-dibutylaminohydroxypropyl ether, hydroxypropylmethyl cellulose, hydroxypropyl cellulose, ethyl cellulose or polyvinyl pyrrolidone, or applying an enteric coating by means of a film-forming agent composed of e.g. ethyl cellulose phthalate cerac, cellulose acetate phthalate or hydroxypropylmethyl cellulose phthalate; granules or fine granules which may be prepared by adding to the active ingredient of the present invention a binder such as starch, gelatin, gum arabic, methyl cellulose, sodium carboxymethyl cellulose, heavy silicic anhydride or light silicic anhydride, followed by kneading and granulation by usual methods; a powder of the active ingredient of the present invention by itself; or capsules which may be prepared by adding to the active ingredient of the present invention an excipient such as lactose, starch or crystalline cellulose and/or a lubricant such as magnesium stearate, calcium stearate or talc, and filling the mixture into capsules. For non-oral administration, an injection formulation may be used wherein an emulsifying agent such as propylene glycol, polyethylene glycol or a vegetable oil such as olive oil, or a solubilization agent such as sodium benzoate, sodium salicylate, N-hydroxyethyl-lactamide, calcium α-saccharide, mannitol, nicotic acid amide or cyclodextrin, is suitably used.

Further, to such formulations, other medicinal substances may be incorporated. Such medicinal substances include, for example, acetazolamide, amiloride, chlorothiazide, furosemide, timolol, propranolol, cetamolol, clonidine, methyldopa, minoxidil, hydralazine, captopril, pivalopril, enalapril, lidinopril, verapamil, nifedipine, nicardipine, felodipine, nimodipine and diltiazem.

An advantageous formulation contains from about 0.1 mg to 500 mg of the compound of the present invention. A preferred range of a daily dose for oral administration is from about 0.1 mg/kg to 500 mg/kg, and such a daily dose may be administered at once or in three times a day. For non-oral administration, it is preferred to administer the compound of the present invention in an amount of from about 0.1 mg/kg to 10 mg/kg per day at once. The dose may be increased or reduced by a doctor's prescription depending upon e.g. the sex and diseased condition of the patient.

Now, the present invention will be described in further detail with reference to the Test Example for renin inhibiting activities of the compounds of the present invention and Working Examples.

TEST EXAMPLE FOR RENIN INHIBITING ACTIVITIES

To 156 μl of a 0.2M sodium phosphate buffer solution (pH7.4), 40 μl of a solution mixture of 34 mM 8-hydroxyquinoline and 100 mM disodium ethylenediaminetetraacetate, 4 μl of dimethyl sulfoxide or a dimethyl sulfoxide solution of an inhibitor and 200 μl of human plasma were added and reacted at 37° C. for one hour. Then, pepstatin was added thereto to terminate the reaction, and the amount of the resulting angiotension I was measured by radio immunoassay whereby the inhibiting activity was determined. The 50% inhibition concentrations ($IC_{50}$ values) of the compounds of the present invention are shown below.

| Compound Name | $IC_{50}$ (mol) |
| --- | --- |
| (2RS,4S,5S)-5-(L-N—benzyloxycarbonylnaphthyl-alanyl-L-norleucyl)amino-4-hydroxy-2-(3-hydroxypropyl)-7-methyl-octanoic acid isobutylamide (compound of Example 14(8)) | $5 \times 10^{-9}$ |
| (2RS,4S,5S)-5-(L-N—benzyloxycarbonylnaphthyl-alanyl-L-norleucyl)amino-4-hydroxy-2-(2-hydroxyethyl)-7-methyl-octanoic acid | $7 \times 10^{-9}$ |

-continued

| Compound Name | $IC_{50}$ (mol) |
| --- | --- |
| isobutylamide (compound of Example 15(3)) | |
| (2RS,4S,5S)-5-(L-N—benzyloxycarbonylnaphthyl-alanyl-L-norleucyl)amino-4-hydroxy-2-isopropyl-7-methyl-octanoic acid isobutylamide (comparative compound) | $4 \times 10^{-8}$ |

Among the compounds disclosed in the above mentioned Japanese Unexamined Patent Publication No. 122,296/1986 and Japanese Unexamined PCT Publication No. 500,415/1986, a derivative having an isopropyl group at the 2-position of the homostatin structure is believed to have the strongest inhibiting activity. Therefore, this derivative i.e. the above-identified comparative compound was synthesized, and the renin inhibiting activity thereof was measured and compared with the activities of the compounds of the present invention. As is evident from the foregoing, the compounds of the present invention have activities higher by about ten times than the comparative compound. Thus, the superiority of the compounds of the present invention have been proven.

Now, the present invention will be described with reference to Examples. However, it should be understood that the present invention is by no means restricted by these specific Examples.

EXAMPLE 1

Statin 111 g of pepstatin was dissolved in 1 liter of concentrated hydrochloric acid and hydrolyzed at a temperature of from 37° C. to 40° C. for two days. The solution was diluted 30 times with 25% water-containing methanol and then passed through a column of Dowex 50 ® (H+-type, 50–100 mesh, 2.5 liters). The column was washed with 5 liters of 25% water-containing methanol and then eluted with 18 liters of 1N aqueous ammonia. The eluate was concentrated to dryness under reduced pressure to obtain 45 g of a crude powder. This powder was dissolved in a 0.2M pyridine/formic acid buffer solution, followed by adsorption on a column of Dowex of 50 ® (pyridine-type, 200–400 mesh, 1.2 liters). The column was washed with 1.5 liters of a 0.2M pyridine/formic acid buffer solution (pH 3.0) and 3.0 liters of a 0.2M pyridine/formic acid buffer solution (pH 4.0) and then eluted with a 0.2M pyridine/formic acid buffer solution (pH 5.0). The statin-containing fraction was collected and concentrated to dryness under reduced pressure to obtain 28 g of statin having the following physical properties.

m.p.: 200°–201° C. (dec.)

$[\alpha]^{20}_D$: −19° (C=0.5, $H_2O$)

$R_f$: 0.49 (silica gel plate, developer: butanol/acetic acid/water (4/1/2))

EXAMPLE 2

N-benzyloxycarbonylstatin 3.0 g of statin was dissolved in a solvent mixture of water/dioxane (1/1), and 5.2 g of benzyl S-4,6-dimethylpyrimidine-2-ylthiolcarbonate and 3.6 ml of triethylamine were added thereto. The mixture was reacted at 30° C. overnight. The reaction solution thus obtained was concentrated, and the residue thereby obtained was dissolved in 100 ml of a 3% sodium hydrogencarbonate and washed twice with 100 ml of ethyl ether. The aqueous layer thus obtained was adjusted to pH 4.0 by a dropwise addition of 1N hydrochloric acid and then extracted twice with 150 ml of ethyl acetate. The ethyl acetate layers were put together and washed once with 0.5N hydrochloric acid and twice with 100 ml of a saturated sodium chloride aqueous solution. The organic layer thus obtained was dried over anhydrous sodium sulfate and concentrated to dryness under reduced pressure. The residue thus obtained was dried under reduced pressure to obtain 4.9 g of N-benzyloxycarbonylstatin as a pale yellow powder having the following physical properties.

m.p.: 118°–121° C.

$[\alpha]^{20}_D$: −43.9° (C=0.90, chloroform)

$R_f$: 0.33 (silica gel plate, developer: chloroform/methanol/33% acetic acid (40/4/1))

| Elemental analysis: As $C_{16}H_{23}NO_5$ | | | |
|---|---|---|---|
| | C % | H % | N % |
| Calculated: | 62.12 | 7.49 | 4.53 |
| Found: | 62.17 | 7.58 | 4.36 |

EXAMPLE 3

Methyl [(4S,5S)-3-benzyloxycarbonyl-2,2-dimethyl-4-isobutyloxazolidin-5-yl]acetate 2.88 g of N-benzyloxycarbonylstatin was dissolved in 15 ml of anhydrous methanol. Then, 0.1 ml of 10% dry hydrochloric acid methanol was added thereto, and the mixture was left to stand at room temperature for 24 hours. Then, 0.1 ml of 10% dry hydrochloric acid methanol was further added thereto, and the mixture was reacted at 40° C. for 24 hours. The reaction solution thus obtained was concentrated, and a syrup thereby obtained was dissolved in a solvent mixture of dichloromethane/toluene, then concentrated and azeotropically dried. The residue thus obtained was dried under reduced pressure to obtain a methyl ester of N-benzyloxycarbonylstatin as a yellow syrup ($R_f$: 0.6, silica gel plate, developer: chloroform/methanol/acetic acid (20/1/0.5)).

This syrup was dissolved in 15 ml of 2,2-dimethoxypropane, and 83 mg of dry p-toluenesulfonic acid was added thereto. The mixture was reacted for 2 hours at room temperature and then one hour at 38° C. The reaction solution thus obtained was diluted with 300 ml of ethyl ether and dried sequentially with a 4% sodium hydrogencarbonate aqueous solution and a saturated sodium chloride aqueous solution. Then, the organic solvent layer was dried over anhydrous sodium sulfate. After filtering the solid off, the filtrate was concentrated and dried to obtain a yellow syrup. The syrup was purified by silica gel column chromatography (developer: toluene/ethyl acetate (20/1)) to obtain 3.08 g (yield: 91%) of methyl [(4S,5S)-3-benzyloxycarbonyl-2,2-dimethyl-4-isobutyloxazolidin-5-yl]acetate as a colorless transparent syrup having the following physical properties.

$[\alpha]^{20}_D$: +8.73° (C=1.03, chloroform)

$R_f$: 0.57 (silica gel plate, developer: benzene/ethyl acetate (9/1))

Mass spectrum: $M^+ + 1 = 364$

EXAMPLE 4

(4S,5S)-3-benzyloxycarbonyl-2,2-dimethyl-5-(2-hydroxyethyl)-4-isobutyloxazolidine 3.02 g of methyl [(4S,5S)-3-benzyloxycarbonyl-2,2-dimethyl-4-isobutyloxazolidin-5-yl]acetate was dissolved in 75 ml of ethanol, and then 630 mg (2 equivalent) of sodium borohydride was added thereto. The mixture was stirred at room temperature for 8 hours. Then, 945 mg of sodium borohydride was added thereto, and the mixture was reacted under the same condition for 16 hours. Then, 945 mg (3 equivalent) of sodium borohydride was further added thereto, and the mixture was reacted under the same condition for 24 hours. The reaction solution thus obtained was concentrated under reduced pressure to obtain a syrup. To this syrup, 250 ml of chloroform and 150 ml of water were added, and about 50 ml of 1N hydrochloric acid was gradually dropwise added under vigorous stirring and cooling with ice to decompose excess sodium borohydride.

The organic solvent layer having a pH of about 5 was separated and washed with 150 ml of a 4% sodium hydrogencarbonate aqueous solution and then with 150 ml of a 10% sodium chloride aqueous solution. The organic solvent layer thus obtained was dried over anhydrous sodium sulfate. Then, after filtering the solid off, the filtrate was concentrated and dried under reduced pressure. The residue thus obtained was dried under reduced pressure to obtain 2.78 g (yield: 99.7%) of (4S,5S)-3-benzyloxycarbonyl-2,2-dimethyl-5-(2-hydroxyethyl)-4-isobutyloxazolidine as a colorless transparent syrup having the following physical properties.

$[\alpha]^{20}_D$: +6.83° (C=0.84, chloroform)

$R_f$: 0.25 (silica gel plate, developer: benzene/ethyl acetate (9/1))

Mass spectrum: $M^+ + 1 = 336$

EXAMPLE 5

(4S,5S)-3-benzyloxycarbonyl-2,2-dimethyl-5-(2-chloroethyl)-4-isobutyloxazolidine 3.89 g of (4S,5S)-3-benzyloxycarbonyl-2,2-dimethyl-5-(2-hydroxyethyl)-4-isobutyloxazolidine was dissolved in 15 ml of pyridine, and 2.65 g of p-toluenesulfonyl chloride was added and dissolved therein. The mixture was then reacted at room temperature overnight. The reaction solution thus obtained was concentrated, and precipitated insolubles were filtered off. The filtrate thus obtained was purified by silica gel column chromatography (developer: benzene/ethyl acetate (30/1)) to obtain 4.47 g of (4S,5S)-3-benzyloxycarbonyl-2,2-dimethyl-5-(2-p-toluenesulfonyloxyethyl)-4-isobutyloxazolidine as a syrup.

This syrup was dissolved in 30 ml of dimethylformamide, and 1.16 g of lithium chloride was added thereto. The mixture was reacted at room temperature overnight. The reaction solution thus obtained was concentrated under reduced pressure, and the residue was dissolved in 300 ml of chloroform. The chloroform solution was washed sequentially with 150 ml of water, a 2% potassium hydrogensulfate aqueous solution, a 4% sodium hydrogencarbonate aqueous solution and a saturated sodium chloride aqueous solution. The organic solvent layer thus obtained was dried over anhydrous sodium sulfate. Then, after filtering the solid off, the filtrate was concentrated under reduced pressure, and the residue thereby obtained was dissolved in 300 ml of chloroform. The chloroform layer was washed sequentially with 150 ml of water, a potassium hydrogensulfate aqueous solution, a 4% sodium hydrogencarbonate aqueous solution and a saturated sodium chloride aqueous solution and then dried over anhydrous sodium sulfate. After filtering the solid off, the filtrate was concentrated under reduced pressure and further dried under reduced pressure to obtain 3.30 g (yield: 80%) of (4S,5S)-3-benzyloxycarbonyl-2,2-dimethyl-5-(2-chloroethyl)-4-isobutyloxazolidine as a colorless transparent syrup having the following physical properties.

$[\alpha]^{20}{}_D$: −8.60 (C=1.29, chloroform)

$R_f$: 0.63 (silica gel plate, developer: benzene/ethyl acetate (9/1)) 0.23 (silica gel plate, developer: hexane/isopropyl ether (4/1))

| Elemental analysis: As $C_{19}H_{28}NO_9Cl$ | | | |
|---|---|---|---|
| | C % | H % | N % | Cl (%) |
| Calculated: | 64.49 | 7.97 | 3.96 | 10.02 |
| Found: | 64.57 | 7.91 | 3.98 | 10.08 |

EXAMPLE 6

(4S,5S)-3-benzyloxycarbonyl-2,2-dimethyl-5-ethenyl-4-isobutyloxazolidine 610 mg of (4S,5S)-3-benzyloxycarbonyl-2,2-dimethyl-5-(2-chloroethyl)-4-isobutyloxazolidine was dissolved in 3.6 ml of dry benzene, and a solution prepared by dissolving 390 mg of potassium tert-butoxide in 3.6 ml of dimethyl sulfoxide, was added thereto. The mixture was reacted at room temperature for 10 minutes. The reaction solution thus obtained was purified by silica gel column chromatography (packed with 36 g of silica gel, developer: benzene/ethyl acetate (30/1)), and the fraction containing the desired compound was collected and concentrated. The residue thus obtained was dried under reduced pressure to obtain 540 mg (yield: 99%) of (4S,5S)-3-benzyloxycarbonyl-2,2-dimethyl-5-ethenyl-4-isobutyloxazolidine as a colorless transparent syrup having the following physical properties.

$R_f$: 0.43 (silica gel plate, developer: hexane/isopropyl ether (4/1))

NMR (60 MHz, CDCl$_3$, δ ppm): 0.7–1.0(m, 6H), 1.1–1.9(m, 3H), 1.5(s, 3H), 1.6(s, 3H), 3.6–4.0(br, 1H), 4.25(dd, 1H, J=4 Hz, 7 Hz), 5.1(s, 2H), 5.0–5.5(ddx2, 2H), 6.0(ddd, 1H, $J_1$-$J_2$=16 Hz, $J_1$-$J_3$=10 Hz, $J_1$-$J_4$=7 Hz), 7.3(s, 5H)

EXAMPLE 7

(4S,5R)-3-benzyloxycarbonyl-2,2-dimethyl-5-formyl-4-isobutyloxazolidine 535 mg of (4S,5S)-3-benzyloxycarbonyl-2,2-dimethyl-5-ethenyl-4-isobutyloxazolidine was dissolved in 3.5 ml of dioxane, and 3 ml of a dioxane solution containing 30 mg of osmium tetraoxide was added thereto. Then, the mixture was reacted for 15 minutes by shutting out light. A brown reaction solution thus obtained was diluted with 7 ml of water, and 4 ml of an aqueous solution containing 720 mg of sodium periodate was gradually dropwise added over a period of one hour under stirring. After completion of the dropwise addition, the stirring was continued for further one hour. Then, after filtering insolubles off, the filtrate was diluted by an addition of 80 ml of ethyl ether. The organic solvent layer was separated and washed twice with 70 ml of a 5% sodium sulfide aqueous solution and then with 70 ml of a 5% sodium chloride aqueous solution. The organic solvent layer thus obtained was dried over anhydrous sodium sulfate. After filtering the solid off, the filtrate was concentrated under reduced pressure. The residue thus obtained was dried under reduced pressure to obtain 540 mg of a crude product of (4S,5R)-3-benzyloxycarbonyl-2,2-dimethyl-5-formyl-4isobutyloxazolidine as a colorless transparent syrup having the following physical properties.

$R_f$: 0.2–0.4, broad (silica gel plate, developer: hexane/ethyl acetate (3/1))

NMR(60 MHz, CDCl$_3$, δ ppm): 0.7–1.1(m, 6H), 1.1–1.6(m, 3H), 1.55(s, 3H), 1.6(s, 3H), 3.6–4.5(br, 2H), 5.1(s, 2H), 7.3(s, 5H), 9.8(s, 1H)

EXAMPLE 8

N-tert-butyloxycarbonylstatin

By using tert-butyl S-4,6-dimethylpyrimidin-2-ylthiolcarbonate, 3.6 g of N-tert-butyloxycarbonylstatin was prepared from 3.0 g of statin in the same manner as in Example 2.

NMR(60 MHz CDCl$_3$, δ ppm): 0.9(d, 6H) 1.4(s, 9H), 1.2–1.6(m, 3H , 2.55(d, 2H), 3.4–4.1(m, 2H), 4.9(m, 1H), 7.4(m, 2H)

EXAMPLE 9

Methyl [(4S,5S)-3-tert-butyloxycarbonyl-2,2-dimethyl-4-isobutyloxazolidin-5-yl]acetate An ethyl ether solution of diazomethane was dropwise added to an ethyl ether solution containing 3.6 g of N-tert-butyloxcarbonylstatin until the yellow color of diazomethane disappeared. Then, the solvent was distilled off under reduced pressure to obtain 3.9 g of a methyl ester of N-tert-butyloxycarbonylstatin. This compound was isopropylidene-modified in the same manner as in Example 3 to obtain 3.64 g of methyl [(4S,5S)-3-tert-butyloxycarbonyl-2,2-dimethyl-4-isobutyloxazolidin-5-yl]acetate.

NMR(60 MHz, CDCl$_3$, δ ppm): 0.95(d, 6H), 1.2–1.7(m, 3H), 1.45(s, 9H), 1.5(s, 3H), 1.6(s, 3H), 2.6(d, 2H), 3.7(s, 3H), 3.7(m, 1H), 4.3(m, 1H)

EXAMPLE 10

(4S,5S)-3-tert-butyloxycarbonyl-2,2-dimethyl-5-(2-hydroxyethyl)-4-isobutyloxazolidine 3.13 g of the compound obtained in Example 9 was reduced in the same manner as in Example 4 to obtain 3.01 g of the above-identified compound.

$R_f$: 0.21 (silica gel plate, developer: hexane/ethyl acetate (3/1))

Mass spectrum: m/z 302(M$^+$+1)

NMR(300 MHz, CDCl$_3$, δ ppm: 0.95(d, 6H), 1.45–1.65(18H), 1.73–1.77(m, H), 1.77–2.0(m, 1H), 2.08(t, 1H), 3.6–3.75(m, 1H), 3.8(dd, 2H), 4.1(m, 1H)

EXAMPLE 11

(4S,5S)-3-tert-butyloxycarbonyl-2,2-dimethyl-5-(2-chloroethyl)-4-isopropyloxazolidine 200 mg of the compound obtained in Example 10 was dissolved in 2 ml of dry methylene chloride, and 115 μl of triethylamine and 152 mg of tosyl chloride were added thereto. The mixture was stirred at room temperature overnight. Then, 115 μl of triethylamine was further added, and the mixture was reacted at room temperature and then evaporated to dryness under reduced pressure. A solution mixture of benzene/ethyl acetate (30/1) was added to the residue. After filtering insolubles off, the filtrate was purified by silica gel column chromatography to obtain 281 mg of (4S,5S)-3-tert-butyloxycarbonyl-2,2-dimethyl-5-(2-p-toluenesulfonyloxyethyl)-4-isobutyloxazolidine as a syrup.

This syrup was treated in the same manner as in Example 5 to obtain 173 mg of the above-identified compound.

$R_f$: 0.43 (silica gel plate, developer: hexane/ethyl aceate(10/1))

NMR(300 MHz, CDCl$_3$, δ ppm) 0.9(d, 6H,), 1.4–1.65(18H), 1.85–2.0(m, 1H), 2.0–2.2(m, 1H), 3.55–3.80(3H), 4.1(m, 1H)

EXAMPLE 12

(4S,5S)-3-tert-butyloxycarbonyl-2,2-dimethyl-5-ethenyl-4-isobutyloxazolidine 1.37 g of (4S,5S)-3-tert-butyloxycarbonyl-2,2-dimethyl-5-(2-chloroethyl)-4-isobutyloxazolidine obtained by the process of Example 11 was treated in the same manner as in Example 6 to obtain 1.14 g of the above-identified compound.

$R_f$: 0.55 (silica gel plate, developer: hexane/ethyl acetate (10/1))

NMR(300 MHz, CDCl$_3$, δ ppm): 0.95(dd, 6H), 1.45–1.65(18H), 3.7–3.9(m, 1H), 4.3(m, 1H), 5.22(d, 1H), 5.33(d, 1H), 6.0(m, 1H)

EXAMPLE 13

(4S,5R)-3-tert-butyloxycarbonyl-2,2-dimethyl-5-formyl-4-isobutyloxazolidine 1.265 g of (4S,5S)-3-tert-butyloxycarbonyl-2,2-dimethyl-5-ethenyl-4-isobutyloxazolidine prepared in accordance with Example 12 was treated in the same manner as in Example 7 to obtain 1.246 g of the above-identified compound.

$R_f$: 0.36 (silica gel plate, developer: hexane/ethyl acetate (3/1))

Mass spectrum: m/z 286(M$^+$+1)

NMR(300 MHz, CDCl$_3$, δ ppm): 0.95(dd, 6H), 1.4–1.7(18H), 4.05–4.3(2H), 9.8(s, 1H)

EXAMPLE 14

(1) L-N-benzyloxycarbonyl leucine 3,5-dimethylpyrazolide 10 g of a piperazine salt of L-N-benzyloxycarbonyl leucine was suspended in 120 ml of 1N hydrochloric acid, and after an addition of 100 ml of ethyl acetate, dissolved under stirring. The aqueous layer was extracted twice with 100 ml of ethyl acetate. The organic layer was washed with a saturated sodium chloride aqueous solution and dried over anhydrous magnesium sulfate. The solvent was distilled off under reduced pressure to obtain an oily substance of L-N-(benzyloxycarbonyl)leucine.

The oily substance thus obtained was dissolved in 85 ml of dry dichloromethane, and 6.89 g of N,N'-dichlorohexylcarbodiimide and 4.38 g of 1-hydroxybenzotriazole were added thereto under stirring and cooling with ice. The mixture was stirred at the same temperature for 20 minutes. Then, 3.21 g of 3,5-dimethylpyrazole was added thereto, and the mixture was stirred at the same temperature for two hours, and then stirred at room temperature overnight. Insolubles were filtered off, and the solvent were distilled off under reduced pressure. The residue was dissolved in 100 ml of ethyl acetate. The ethyl acetate solution was washed sequentially with a 10% citric acid aqueous solution, water, a 4% sodium hydrogencarbonate aqueous solution, water and a saturated sodium chloride aqueous solution and dried over anhydrous magnesium sulfate. The solvent was distilled off under reduced pressure, and the residue was recrystallized from hexane/ethyl acetate to obtain 7.08 g of L-N-benzyloxycarbonyl leucine 3,5-dimethylpyrazolide as colorless needle-like crystals.

m.p.: 88°–89° C.

$[α]^{20}_D$: +10.57° (C=0.95, acetic acid)

$R_f$: 0.76 (silica gel plate, developer: chloroform methanol (50/1))

(2)

2(s)-2-benzyloxycarbonylamino-1-hydroxy-4-methyl-hexanenitrile (a) 860 mg of lithium aluminum hydride was suspended in 15 ml of dry tetrahydrofuran under nitrogen. A solution prepared by dissolving 6.98 g of pyrazolide in 80 ml of dry tetrahydrofuran, was dropwise added over a period of 50 minutes under stirring at −20° C. The mixture was stirred at the same temperature for one hour, and then 5 ml of 5N hydrochloric acid was added. Insolubles were filtered off, and the solvent was distilled off under reduced pressure. The residue was dissolved in 100 ml of diethyl ether. The diethyl ether solution was washed sequentially with 1N hydrochloric acid, water and a saturated sodium chloride aqueous solution and dried over anhydrous magnesium sulfate. The solvent was distilled off under reduced pressure to obtain L-N-benzyloxycarbonyl leucinal as an anhydrous oily substance.

$R_f$: 0.63 (silica gel plate, developer: chloroform/methanol (10/1))

(b) Then, L-N-benzyloxycarbonyl leucinal was suspended in 15 ml of an aqueous solution containing 2.12 g of sodium hydrogensulfite and stirred at room temperature overnight. After an addition of 80 ml of ethyl acetate thereto, 25 ml of an aqueous solution containing 1.01 g of sodium cyanide was dropwise added over a period of 2 hours. The mixture was stirred at room temperature for 3 hours, and then the organic layer was washed sequentially with water and a saturated sodium chloride aqueous solution and dried over anhydrous magnesium sulfate. The solvent was distilled off under reduced pressure to obtain 5.16 g of the above-identified compound as a colorless oily substance.

$R_f$: 0.57 (silica gel plate: developer: chloroform/methanol (10/1))

(3) (2RS,3S)-3-amino-2-hydroxy-5-methyl-hexanoic acid 5.16 g of cyanohydrin was dissolved in a mixture of dioxane (55 ml)/concentrated hydrochloric acid (55 ml)/anisole (24 ml), and the mixture was refluxed under heating at 110° for 10 hours. The reaction mixture was washed with 80 ml of ethyl acetate, and then the aqueous solution was distilled off under reduced pressure. The residue was dissolved in a small amount of water and passed through a cation exchange resin Dowex ® 50W×2 (100−200 mesh, H$^+$-type, 40 ml). After washing with water, the adsorbed portion was eluted with 1N aqueous ammonia (150 ml). The product-containing fraction was subjected to distillation under reduced pressure. The residue was crystallized from acetone to obtain 1.9 g of (2RS,3S)-3-amino-2-hydroxy-5-methylhexanoic acid as a colorless powder.

$R_f$: 0.41 (silica gel plate, developer: n-butanol/acetic acid/water (4/1/1))

(4)
(2R,3S)-3-benzyloxycarbonylamino-2-hydroxy-5-methylhexanoic acid 3,5-dimethylpyrazolide (a) 1 g of (2RS,3S)-3-amino-2-hydroxy-5-methylhexanoic acid was suspended in 5 ml of water and, after an addition of 1.7 ml of triethylamine, dissolved. Then, a solution prepared by dissolving 1.88 g of S-(benzyloxycarbonyl)-4,6-dimethyl-2-thiopyrimidine in 5 ml of dioxane, was added thereto, and the mixture was stirred at room temperature overnight. 30 ml of water was added to the reaction mixture, and then the mixture was washed twice with 50 ml of ethyl acetate. The aqueous layer was adjusted to pH 2.0 with 5N hydrochloric acid under cooling with ice and extracted three times with 30 ml of ethyl acetate. The ethyl acetate layer was washed with 1N hydrochloric acid and a saturated sodium chloride aqueous solution and then dried over anhydrous magnesium sulfate. The solvent was distilled off under reduced pressure to obtain 1.3 g of (2RS,3S)-3-benzyloxycarbonylamino2-hydroxy-5-methylhexanoic acid as a colorless oily substance.

$R_f$: 0.29 (silica gel plate, developer: chloroform/methanol/acetic acid (10/1/0.5))

(b) 1.3 g of (2RS,3S)-3-benzyloxycarbonylamino-2-hydroxy-5-methyl-hexanoic acid was dissolved in 13 ml of dry dichloromethane, and 455 mg of 3,5-dimethylpyrazole, 623 mg of 1-hydroxybenzotriazole and 968 mg of N,N'-dicyclohexylcarbodiimide were added thereto at −10° C. under stirring. The mixture was stirred at the same temperature for 2 hours and then, stirred at room temperature overnight. After filtering insolubles off, the solvent was distilled off under reduced pressure. The residue was dissolved in 30 ml of ethyl acetate. The ethyl acetate solution was washed sequentially with a 10% citric acid aqueous solution, water, a 4% sodium hydrogencarbonate aqueous solution, water and a saturated sodium chloride aqueous solution and dried over anhydrous magnesium sulfate. The solvent was distilled off under reduced pressure, and the residue was purified by silica gel column chromatography (20 g of Kieselgel 60 by using chloroform to obtain 1.4 g of dimethylpyrazolide as a colorless oily substance).

860 mg of dimethylpyrazolide was further separated and purified by silica gel column chromatography (30 g of Kieselgel 60) to obtain 427 mg of (2S,3S)-3-benzyloxycarbonylamino-2-hydroxy-5-methylhexanoic acid 3,5-dimethylpyrazolide from the fraction eluted with hexane/ethyl acetate (9/1) and 110 mg of the above-identified compound from the fraction eluted with hexane/ethyl acetate (5/1), respectively, as oily substances.

$R_f$: 0.23, 0.16 (silica gel plate, developer: hexane/ethyl acetate (5/1))

(5)
(2RS,3S)-benzyloxycarbonylamino-2-(2-tetrahydropyranyloxy)-5-methylhexanal (a) 162 mg of (2RS,3S)-3-benzyloxycarbonylamino-2-hydroxy-5-methylhexanoic acid 3,5-dimethylpyrazolide was dissolved in 1 ml of dry dichloromethane, and 102 μl of dihydropyran and 0.8 mg of p-toluenesulfonic acid monohydrate were added thereto. The mixture was stirred at room temperature for 1.5 hours. Then, 10 ml of chloroform was added to the mixture, and the mixture was washed with a 4% sodium hydrogencarbonate and a saturated sodium chloride aqueous solution and dried over anhydrous magnesium sulfate. Then, the solvent was distilled off under reduced pressure to obtain 207 mg of (2RS,3S)-3-benzyloxycarbonylamino-2-(2-tetrahydropyranyloxy)-5-methylhexanoic acid 3,5-dimethylpyrazolide as a colorless oily substance.

$R_f$: 0.36, 0.30 (silica gel plate, developer: hexane/ethyl acetate (4/1))

(b) 18 mg of lithium aluminum hydride was suspended in 0.3 ml of dry tetrahydrofuran under nitrogen. A solution prepared by dissolving 207 mg of the tetrahydropyranyl compound in 2.3 ml of dry tetrahydrofuran was dropwise added at −20° C. under stirring. The mixture was further stirred at the same temperature for 1.25 hours, and then 0.1 ml of 5N hydrochrolic acid was added thereto. Insolubles were filtered off, and the solvent was distilled off under reduced pressure. The residue was dissolved in diethyl ether. The diethyl ether solution was washed sequentially with 1N hydrochloric acid, water and a saturated sodium chloride aqueous solution and dried over anhydrous magnesium sulfate. The solvent was distilled off under reduced pressure to obtain 118 mg of the above-identified compound as a colorless oily substance.

$R_f$: 0.30, 016 (silica gel plate, developer: hexane/ethyl acetate (3/1))

(6) Ethyl 2-diethylphosphono-5-(2-tetrahydropyranyloxy)heptanoate 0.58 ml of 3-bromo-1-propanol was dissolved in 6 ml of dry dichloromethane, and 1.22 ml of dihydropyran and 10 mg of dry p-toluenesulfonic acid were added thereto. The mixture was stirred at room temperature overnight, and the mixture was partitioned with 30 ml of chloroform and 15 ml of a 4% sodium hydrogencarbonate aqueous solution. The organic solvent layer was washed with water and dried over anhydrous magnesium sulfate. The solvent was distilled off under reduced pressure. The residue was separated by silica gel column chromatography (10 g of Kieselgel 60) by using chloroform. Then, the fraction containing the product was purified by silica gel column chromatography (10 g of Kieselgel 60) by using a mixture of n-hexane/ethyl acetate (20/1). The fractions containing the product were put together, and the solvent was distilled off under reduced pressure to obtain 1.44 g of 3-bromo-1-(2-tetrahydropyranyloxy)propane as a colorless oily substance.

$R_f$: 0.33 (silica gel plate, developer: hexane/ethyl acetate (10/1))

215 mg of a sodium hydride dispersion (50% in oil) was washed three times with hexane under argon in an Erlenmeyer flask, and the oil was separated. After drying, the powder thereby obtained was suspended in 1.5 ml of dry dimethylformamide under an argon gas stream, and the suspension was cooled to 0° C. Then, 0.9 ml of ethyl diethylphosphonoacetate was dropwise added to the mixture over a period of one hour. The mixture was stirred at room temperature for 30 minutes and then cooled to 0° C., and 1.23 g of 3-bromo-1-(2-tetrahydropyranyloxy)propane was added thereto. The mixture was stirred at room temperature overnight and then stirred at 65° C. for 8 hours. The mixture was poured into 15 ml of water and extracted three times with 20 ml of chloroform. The organic solvent layer was washed with water and dried over anhydrous magnesium sulfate. The solvent was distilled off under reduced pressure. The residue was separated by silica gel column chromatography (10 g of Kieselgel 60) by using a mixture of n-hexane/ethyl acetate (2/1). The product-containing fraction was purified again by silica gel column chromatography (8 g of Kieselgel) to obtain 583 mg of ethyl 2-diethylphosphono-5-(2-tetrahydropyranyloxy)heptanoate as a colorless oily substance.

Mass spectrum: m/z 367 (M$^+$ +1)

R$_f$: 0.33 (silica gel plate, developer: hexane/ethyl acetate (1:5))

(7)
(2RS,4S,5S)-5-amino-4-hydroxy-2-[3-(2-tetrahydropyranyloxy)propyl]-7-methyl-octanoic acid isobutylamide (a) 63.4 mg of lithium chloride was suspended in 5 ml of dry tetrahydrofuran under an argon gas stream. A solution prepared by dissolving 546 mg of ethyl 2-diethylphosphono-5-(2-tetrahydropyranyloxy)heptanoate in 0.6 ml of dry tetrahydrofuran, was added thereto under stirring. The mixture was stirred for five minutes at room temperature, and then 1.4 ml of a 20% dry tetrahydrofuran solution of diazabicycloundecene was added. The mixture was stirred for 10 minutes at room temperature. Then, a solution prepared by dissolving 396 mg of (4S,5R)-3-benzyloxycarbonyl-2,2-dimethyl-5-formyl-4-isobutyloxazolidine in 1.0 ml of dry tetrahydrofuran, was added thereto, and the mixture was stirred overnight at room temperature. The mixture was cooled to 0° C. and then neutralized with 1N hydrochloric acid. Insolubles were filtered off, and the solvent was distilled off under reduced pressure. The residue was dissolved in 20 ml of ethyl acetate and washed with water. The aqueous layer was further extracted twice with 15 ml of ethyl acetate. The ethyl acetate layer was dried over anhydrous magnesium sulfate. The solvent was distilled off under reduced pressure, and the residue was purified by silica gel column chromatography (8 g of Kieselgel 60) by using a mixture of hexane/ethyl acetate (10/1) to obtain 556 mg of ethyl 3-[(4S,5S)-3-benzyloxycarbonyl-2,2-dimethyl-4-isobutyloxazolidine- 5-yl]-2-[3-(2-tetrahydropyranyloxy)propyl]-2-propenoate (E/Z (60/40)) as a colorless oily substance.

R$_f$: 0.51 (silica gel plate, developer: hexane/ethyl acetate (10/1))

(b) 100 mg of ethyl 3-[(4S,5S)-3-benzyloxycarbonyl-2,2-dimethyl-4-isobutyloxazolidine-5-yl]-2-[3-(2-tetrahydropyranyloxy)propyl]-2-propenoate was dissolved in 0.2 ml of ethanol, and 0.5 ml of an ethanol/water (10/1) solution of 2N potassium hydroxide was added thereto under stirring. The mixture was stirred overnight at room temperature, then cooled to 0° C. and neutralized with 1N hydrochloric acid. To the mixture, 12 ml of water was added, and the mixture was extracted three times with 12 ml of ethyl acetate. The ethyl acetate layer was washed sequentially with water and a saturated sodium chloride aqueous solution and then dried over anhydrous magnesium sulfate. Then, the solvent was distilled off under reduced pressure to obtain 3-[(4S,5S)-3-benzyloxycarbonyl-2,2-dimethyl-4-isobutyloxazolidine-5-yl]-2-[3-(2-tetrahydropyranyloxy)propyl]-2-propenoic acid as a colorless oily substance.

Without purification, this propenoic acid was dissolved in 1 ml of dry dimethylformamide, and 30 μl of triethylamine, 50 μl of diphenylphosphorylazide and 20 μl of isobutylamine were added thereto at −20° C. under stirring. After stirring overnight at room temperature, 30 ml of ethyl acetate was added thereto. The ethyl acetate layer was washed sequentially with water and a saturated sodium chloride aqueous solution and dried over anhydrous magnesium sulfate. The solvent was distilled off under reduced pressure, and the residue was purified by silica gel column chromatography (2 g of Kieselgel 60) by using a mixture of hexane/ethyl acetate (3/1) to obtain 75 mg of 3-[(4S,5S)-3-benzyloxycarbonyl-2,2-dimethyl-4-isobutyloxazolidine-5-yl]-2-[3-(2-tetrahydropyranyloxy)propyl]-2-propenoic acid isobutylamide as colorless oily substance.

R$_f$: 0.26 (silica gel plate, developer: hexane/ethyl acetate (2/1))

(c) 75 mg of 3-[4S,5S)-3-benzyloxycarbonyl-2,2-dimethyl-4-isobutyloxazolidine-5-yl]-2-[3-(2-tetrahydropyranyloxy)propyl]-2-propenoic acid isobutylamide was dissolved in 1.7 ml of methanol and hydrogenated by using palladium black under atmospheric pressure. The reaction mixture was subjected to filtration, and the solvent was distilled off from the filtrate under reduced pressure to obtain (2RS,4S,5S)-5-amino-4-hydroxy-2-[3-(2-tetrahydropyranyloxy)propyl]-7-methyl-octanoic acid isobutylamide as a colorless oily substance.

R$_f$: 0.62 (silica gel plate, developer: chloroform/methanol/aqueou ammonia (10/2/0.2))

(8)
(2RS,4S,5S)-5-(L-N-benzyloxycarbonylnaphthylalanyl-L-norleucyl)amino-4-hydroxy-2-(3-hydroxypropyl)-7-methyl-octanoic acid isobutylamide (a) 59.9 mg of L-N benzyloxycarbonylnaphthylalanyl-L-norleucine was dissolved in 0.5 ml of dry dimethylformamide. Then, 22 μl of triethyamine, 34 μl of diphenylphosphorylazide and a solution prepared by dissolving 51 mg of (2RS,4S,5S)-5-amino-4-hydroxy-2-[3-(2-tetrahydropyranyloxy)propyl]-7-methyl-octanoic acid isobutylamide in 0.5 ml of dry dimethylformamide, were added thereto at −20° C. under stirring. The mixture was stirred overnight at room temperature, and then 25 ml of ethyl acetate was added thereto. The ethyl acetate layer was washed sequentially with a 10% citric acid aqueous solution, water, a 4% sodium hydrogencarbonate aqueous solution, water and a saturated sodium chloride aqueous solution and then dried over anhydrous magnesium sulfate. The solvent was distilled off under reduced pressure, and the residue was purified by silica gel column chromatography (4 g of Kieselgel 60) by using a mixture of chloroform/methanol (40/1) to obtain 79.5 mg of (2RS,4S,5S)-5-(L-N-benzyloxycarbonylnaphthylalanyl-L-norleucyl)amino-4-hydroxy-2-[3-(2-tetrahydropyranyloxy)propyl]-7-methyl-octanoic acid isobutylamide as an oily substance.

R$_f$: 0 13 (silica gel plate, developer: chloroform/methanol (30/1))

(b) 79.5 mg of (2RS,4S,5S)-5-(L-N-benzyloxycarbonylnaphthylalanyl-L-norleucyl)amino-4-hydroxy-2-[3-(2-tetrahydropyranyloxy propyl]-7-methyl-octanoic acid isobutylamide was dissolved in 3 ml of a mixture of methanol/ethyl acetate (2/1), and 0.35 ml of 1N hydrochloric acid was added thereto under stirring. The mixture was stirred at room temperature for 2 hours, and then 10 ml of water was added. The aqueous solution was extracted three times with 15 ml of ethyl acetate, and the ethyl acetate layer was washed sequentially with water and a saturated sodium chloride aqueous solution and then dried over anhydrous magnesium sulfate. Then, the solvent was distilled and under reduced pressure. The residue was crystallized by using methanol/water to obtain 59.3 mg of the above-identified compound as a crystalline powder.

$R_f$: 0.43, 0.40 (silica gel plate, developer: chloroform/methanol (10/1))

Mass spectrum m/z 747 (M+ +1)

NMR(300 MHz, CDCl$_3$, δ ppm): 0.82(6H, d, J=6.3 Hz), 0.851(3H, t, J=6.6 Hz), 0.852(6H, d, J=6.0 Hz), 1.03–1.78(16H, m), 2.18–2.45(1H, m), 2.89–3.08(2H, m), 3.28–3.62(5H, m), 3.66–3.89(1H, m), 4.10–4.20(1H, m), 4.45–4.58(1H, m), 4.96(2H, s), 7.14–7.37(7H, m), 7.37–7.58(2H, m), 7.72(1H, d, J=8.1Hz), 7.82(1H, d, J=8.7 Hz, 8.10(1H, d, J=8.4 Hz)

EXAMPLE 15

(1) Ethyl 2-diethylphosphono-4-(2-tetrahydropyranyloxy)-butanoate (a) 2.29 ml of 2-bromoethanol was dissolved in 27.8 ml of dry dichrolomethane, and 7.21 ml of dihydropyran and then 48.1 mg of dry p-toluenesulfonic acid were added thereto. The mixture was stirred at room temperature for 3 hours. Then, the reaction mixture was partitioned with 150 ml of chloroform and 75 ml of a 4% sodium hydrogen-carbonate aqueous solution. The organic layer was washed sequentially with water and a saturated sodium chloride aqueous solution and then dried over anhydrous sodium sulfate. The solvent was distilled off under reduced pressure, and the residue was purified by silica gel column chromatography (50 g of Kieselgel 60) by using a mixture of hexane/ethyl acetate (20/1). The product-containing fractions were put together, and the solvent was distilled off under reduced pressure to obtain 5.4 g of 2-bromo-1-(2-tetrahydropyranyloxy)ethane as a oily substance.

$R_f$: 0.35 (silica gel plate, developer: hexane/ethyl acetate (10/1))

(b) 856 mg of a sodium hydride dispersion (60% in oil) was washed three times with dry pentane under a nitrogen stream to separate the oil. After drying, the powder obtained was suspended in 7.2 ml of dry dimethylformamide under a nitrogen stream, and the suspension was cooled to 0° C. Then, 4.26 ml of ethyl diethylphosphonoacetate was dropwise added thereto over a period of one hour. The mixture was stirred at room temperature for 30 minutes and cooled to 0° C., and 5.4 g of 2-bromo-1-(2-tetrahydropyranyloxy)ethane was added thereto. The mixture was stirred at 65° C. overnight, and the reaction mixture was poured into 40 ml of water and extracted three times with 20 ml of ethyl acetate. The ethyl acetate layer was washed sequentially with water and a saturated sodium chloride aqueous solution and then dried over anhydrous sodium sulfate. The solvent was distilled off under reduced pressure, and the residue was separated by silica gel column chromatography (60 g of Kieselgel 60) by using a mixture of hexane/ethyl acetate (5/1 followed by 1/1). The product-containing fraction was again purified by silica gel column chromatography (110 g of Kieselgel 60) by using a mixture of hexane/acetone (4/1) to obtain 2.55 g of ethyl 2-diethylphosphono-4-(2-tetrahydropyranyloxy)butanoate as a colorless oily substance.

$R_f$: 0.28 (silica gel plate, developer: hexane/ethyl acetate (1/5))

(2) (2RS,4S,5S)-5-amino-4-hydroxy-2-[2-(2-tetrahydropyranyloxy)ethyl]-7-methyl-octanoic acid isobutylamide (a) 79.6 mg of lithium chloride was suspended in 5 ml of dry tetrahydrofuran under an argon atmosphere. Then, a solution prepared by dissolving 670 mg of ethyl 2-diethylphosphono-4-(2-tetrahydropyranyloxy)-butanoate in 0.6 ml of dry tetrahydrofuran, was added thereto under stirring. The mixture was stirred for 5 minutes at room temperature, and then 1.75 ml of a 20% dry tetrahydrofuran solution of diazabicycloundecene was added thereto. The mixture was stirred for 10 minutes at room temperature. Then, a solution prepared by dissolving 506 mg of (4S,5R)-3-benzyloxycarbonyl-2,2-dimethyl-5-formyl-4-isobutyloxazolidine in 1.0 ml of dry tetrahydrofuran, was added thereto, and the mixture was stirred overnight at room temperature. The reaction mixture was cooled to 0° C. and neutralized with 1N hydrochloric acid. Then, the mixture was extracted three times with ethyl acetate, and the ethyl acetate layer was washed sequentially with water and a saturated sodium chloride aqueous solution and then dried over anhydrous sodium sulfate. The solvent is distilled off under reduced pressure, and the residue was purified by silica gel column chromatography (20 g of Kieselgel 60) by using a mixture of hexane/ethyl acetate (10/1) to obtain 550 mg of ethyl 3-[(4S,5S)-3-benzyloxycarbonyl-2,2-dimethyl-4-isobutyloxazolidin-5-yl]-2-[2-(2-tetrahydropyranyloxy)ethyl]-2-propenoate (E/Z (50/50)) as a colorless oily substance.

$R_f$: 0.21 (silica gel plate, developer: hexane/ethyl acetae (5/1))

(b) 400 mg of ethyl 3-[(4S,5S)-3-benzyloxycarbonyl-2,2-dimethyl-4-isobutyloxazolidin-5-yl]-2-[2-(2-tetrahydropyranyloxy)ethyl]-2-propenoate was dissolved in 1.93 ml of an ethanol/water (10/1) solution of 2N potassium hydroxide, and the solution was stirred overnight at room temperature. 24 ml of water was added thereto, and the mixture was cooled to 0° C., then neutralized with 1N hydrochloric acid and extracted three times with 15 ml of ethyl acetate. The ethyl acetate layer was washed sequentially with water and a saturated sodium chloride aqueous solution and then dried over anhydrous sodium sulfate. Then the solvent was distilled off under reduced pressure to obtain 3-[(4S,5S)-3-benzyloxycarbonyl-2,2-dimethyl-4-isobutyloxazolidin-5yl]-2-[2-(2-tetrahydropyranyloxy)ethyl]-2-propenoic acid as a colorless oily substance.

The residue was dissolved in 1 ml of dry dimethylformamide, and 85.6 μl of isobutylamine, 189 μl of diphenylphosphorylazide and 122 μl of triethylamine were added thereto at −10° C. under stirring. The mixture was stirred at −10° C. for one hour and at room temperature overnight. Then, 60 ml of ethyl acetate was added. The ethyl acetate layer was washed sequentially with a 10% citric acid aqueous solution, water, a 4% sodium hydrogen carbonate aqueous solution, water and a saturated sodium chloride aqueous solution and then dried over anhydrous sodium sulfate. The solvent was distilled off under reduced pressure, and the residue was purified by silica gel column chromatography (20 g of Kieselgel 60) by using a mixture of hexane/ethyl acetate (4/1) to obtain 364 mg of 3-[(4S,5S)-3-benzyloxycarbonyl-2,2-dimethyl-4-isobutyloxazolidin-5-yl]-2-[2-(2-tetrahydropyranyloxy)ethyl]-2-propenoic acid isobutylamide as a colorless oily substance.

$R_f$: 0.19 (silica gel plate, developer: hexane/ethyl acetate (5/2))

(c) 101 mg of 3-[(4S,5S)-3-benzyloxycarbonyl-2,2-dimethyl-4-isobutyloxazolidin-5-yl]-2-[2-(2-tetrahydropyranyloxy)ethyl]-2-propenoic acid isobutylamide in 1 ml of ethanol and hydrogenated by using palladium black under atmospheric pressure. The reaction mixture was subjected to filtration, and the solvent was distilled off from the filtrate under reduced pressure to obtain 64 mg of (2RS,4S,5S)-5-amino-4-hydroxy-2-[2-(2-tetrahydropyranyloxy)ethyl]-7-methyl-octanoic acid isobutylamide as a colorless oily substance.

$R_f$: 0.22 (silica gel plate, developer: chloroform/methanol/aqueous ammonia (10/0.5/0.2))

(3)
(2RS,4S,5S)-5-(L-N-benzyloxycarbonylnaphthylalanyl-L-norleucyl)amino-4-hydroxy-2-(2-hydroxyethyl)-7-methyloctanoic acid isobutylamide (a) 64 mg of 2RS,4S,5S)-5-amino-4-hydroxy-2-[2-(2-tetrahydropyranyloxy)ethyl]-7-methyl-octanoic acid isobutylamide was dissolved in 0.5 ml of dry dimethylformamide, and 80 mg of L-N-benzyloxycarbonylnaphthylalanyl-L-norleucine, 45 μl of diphenylphosphorylazide and 29 μl of triethylamine were added thereto at −10° C. under stirring. Then, the mixture was stirred at −10° C. for one hour and then at room temperature overnight. Then, 50 ml of ethyl acetate was added thereto. The ethyl acetate layer was washed sequentially with a 10% citric acid aqueous solution, water, a 4% sodium hydrogencarbonate aqueous solution, water and a saturated sodium chloride aqueous solution and then dried over anhydrous sodium sulfate. The solvent was distilled off under reduced pressure, and the residue was purified by silica gel column chromatography (5 g of Kieselgel 60) by using a mixture of chloroform/methanol (40/1) to obtain 77 mg of (2RS,4S,5S)-5-(L-N-benzyloxycarbonylnaphthylalanyl-L-norleucyl)amino-4-hydroxy-2-[2-(2-tetrahydropyranyloxy)ethyl]-7-methyl-octanoic acid isobutylamide as a colorless powder.

$R_f$: 0.38 (silica gel plate, developer: chloroform/methanol (20/1))

Mass spectrum: m/z 818 (M$^+$+1)

(b) 76 mg of (2RS,4S,5S)-5-(L-N-benzyloxycarbonylnaphthylalanyl-L-norleucyl)amino-4-hydroxy-2-[2-(2-tetrahydropyranyloxy)ethyl]-7-methyl-octanoic acid isobutylamide was dissolved in 1.8 ml of a mixture of methanol/ethyl acetate (5/4), and 0.2 ml of 1N hydrochloric acid was added thereto under stirring. The mixture was stirred at room temperature for 2 hours, and then 10 ml of water was added thereto. The aqueous layer was extracted once with 30 ml and twice with 15 ml of ethyl acetate. The ethyl acetate layer was washed sequentially with water and a saturated sodium chloride aqueous solution and then dried over anhydrous magnesium sulfate. Then, the solvent was distilled off under reduced pressure, and the residue was crystallized by using methanol/water to obtain 66 mg of the above-identified compound as crystalline powder.

$R_f$: 0.47, 0.55 (silica gel plate, developer: chloroform/methanol (10/1))

Mass spectrum: m/z 733 (M$^+$+1)

NMR(300 MHz, CD$_3$OD, δ ppm): 0.85–0.95(15H, m), 1.2–1.78(14H, m), 2.44–2.71(1H, m), 2.89–3.04(2H, m), 3.4–3.6(3H, m), 3.65–3.75(1H, m), 3.85–3.98(1H, m), 4.25–4.37(1H, m), 4.52–4.63(1H, m), 4.96(2H, s), 7.15–7.42(7H, m), 7.43–7.6(2H, m), 7.75(1H, dd, J=3.0 Hz, 6.4 Hz), 7.85(1H, d, J=8.1Hz), 8.18(1H, d, J=8.6 Hz)

EXAMPLE 16

(1) Ethyl 2-diethylphosphono-4,5-O-isopropylidene heptanoate (a) 2.3 g of 3-bromo-1,2-propanediol was dissolved in 11 ml of 2,2-dimethoxypropane, and 125 mg of dry p-toluenesulfonic acid was added thereto. The mixture was stirred overnight at room temperature, and the reaction solution was purified by silica gel column chromatography (90 g of Kieselgel 60) by using hexane/ethyl acetate (20/1) to obtain 2.02 g of 3-bromo-1,2-O-isopropylidene propane as a pale yellow oily substance.

$R_f$: 0.63 (silica gel plate developer: hexane/ethyl acetate (5/1))

(b) 428 g of a sodium hydride dispersion (50% in oil) was washed with hexane under an argon stream to separate the oil. After drying, the powder obtained was suspended in 3.0 ml of dry dimethylformamide under an argon stream, and the dispersion was cooled to 0° C. Then, 1.8 ml of ethyl diethylphosphono acetate was dropwise added over a period of 30 minutes. The mixture was stirred at room temperature for one hour and then cooled to 0° C. Then, a solution prepared by dissolving 1.97 g of 3-bromo-1,2-O-isopropylidene propane in 0.8 ml of dry dimethylformamide, was added thereto. The mixture was stirred overnight at 65° C. Then, the reaction mixture was poured into 20 ml of water and extracted three times with 20 ml of ethyl acetate. The ethyl acetate layer was washed sequentially with water and a saturated sodium chloride aqueous solution and then dried over anhydrous magnesium sulfate. Then, the solvent was distilled off under reduced pressure, and the residue was purified by silica gel column chromatography (20 g of Kieselgel 60) by using hexane/ethyl acetate (2/1) to obtain 760 mg of the above-identified compound as a colorless oily substance.

$R_f$: 0.49 (silica gel plate, developer: hexane/ethyl acetate (1/5))

(2)
(2RS,4S,5S)-5-amino-4-hydroxy-2-(2,3-O-isopropylidenepropyl)-7-methyl-octanoic acid isobutylamide (a) 68.6 mg of lithium chloride was suspended in 5 ml of dry tetrahydrofuran in an argon stream, and a solution prepared by dissolving 461 mg of ethyl 2-diethylphosphono-4,5-O-isopropylideneheptanoate in 0.6 ml of dry tetrahydrofuran, was added thereto under stirring. The mixture was stirred for 5 minutes at room temperature, and then 1.4 ml of a 20% dry tetrahydrofuran solution of diazabicycloundecene was added thereto. The mixture was stirred for 10 minutes at room temperature. Then, a solution prepared by dissolving 408 mg of (4S,5R)-3-benzyloxycarbonyl-2,2-dimethyl-5-formyl-4-isobutyloxazolidine in 1.0 ml of dry tetrahydrofuran was added thereto, and the mixture was stirred overnight at room temperature. The reaction mixture was cooled to 0° C. and neutralized with 1N hydrochloric acid. Insolubles was filtered off, and the solvent was distilled off under reduced pressure. The residue was dissolved in 30 ml of ethyl acetate and then washed with water. The aqueous layer was extracted further with 20 ml of ethyl acetate. The ethyl acetate layer was washed sequentially with water and a saturated sodium chloride aqueous solution, and then dried over anhydrous magnesium sulfate. The solvent was distilled off under reduced pressure, and the residue was purified by silica gel column chromatography (8 g of Kezelgale 60) by using hexane/ethyl acetate (10/1) to obtain 115 mg of the E-isomer, 179 mg of the Z-isomer and 46 mg of a EZ-mixture of ethyl 3-[(4S,5S)-3-benzyloxycarbonyl-2,2-dimethyl 4-isobutyloxazolidin-5-yl]-2-(2,3-O-isopropylidenepropyl)-2-propenoate, respectively, as colorless oily substances.

$R_f$: E-isomer 0.43, Z-isomer 0.38 (silica gel plate, developer: hexane/ethyl acetate (3/1))

(b) 115 mg of ethyl 3-[(4S,5S)-3-benzyloxycarbonyl-2,2-dimethyl-4-isobutyloxazolidin-5-yl]-2-(2,3-O-isopropylidenepropyl)-2-propenoate (EZ-mixture) was dissolved in 0.3 ml of ethanol, and 0.57 ml of an ethanol/water (10/1) solution of 2N potassium hydroxide was added thereto under stirring. The mixture was stirred overnight at room temperature, then cooled to 0° C. and neutralized with 1N hydrochloric acid. Then, 10 ml of water was added to the reaction mixture, and the mixture was extracted three times with 10 ml of ethyl acetate. The ethyl acetate layer was washed sequentially with water and a saturated sodium chloride aqueous solution, and then dried over anhydrous magnesium sulfate. The solvent was distilled off under reduced pressure to obtain 3-[(4S,5S)-3-benzyloxycarbonyl-2,2-dimethyl-4-isobutyloxazolidin-5-yl]-2-(2,3-O-isopropylidenepropyl)-2-propenoic acid as a colorless oily substance.

Without purification, the propenoic acid was dissolved in 1 ml of dimethylformamide, and 38 μl of triethylamine, 60 μl of diphenylphosphorylazide and 27 μl of isobutylamine were added thereto at −20° C. under stirring. The mixture was stirred overnight at room temperature, and then, 30 ml of ethyl acetate was added thereto. The ethyl acetate layer was washed sequentially with water and a saturated sodium chloride aqueous solution and then dried over anhydrous magnesium sulfate. The solvent was distilled off under reduced pressure and the residue was purified by silica gel column chromatography (2 g of Kieselgel of 60) by using hexane/ethyl acetate (5/1) to obtain 98 mg of 3-[(4S,5S)-3-benzyloxycarbonyl-2,2-dimethyl-4-isobutyloxazolidin-5-yl]-2-(2,3-O-isopropylidenepropyl)-2-propenoic acid isobutylamide as a colorless oily substance.

$R_f$: 0.20 (silica gel plate, developer: hexane/ethyl acetate (3/1))

(c) 93 mg of 3-[(4S,5S)-3-benzyloxycarbonyl-2,2-dimethyl-4-isobutyloxazolidin-5-yl]-2-(2,3-O-isopropylidenepropyl)-2-propenoic acid isobutylamide was dissolved in 1.5 ml of ethanol and then hydrogenated by using palladium black under atmospheric pressure. The reaction mixture was subjected to filtration, and the solvent was distilled off from the filtrate under reduced pressure to obtain 67 mg of the above-identified compound as a colorless oily substance.

$R_f$: 0.61 (silica gel plate, developer: chloroform/methanol/ammonia (10/2/0.2))

(3)
(2RS,4S,5S)-5-(L-N-benzyloxycarbonylnaphthylalanyl-L-norleucyl)amino-4-hydroxy-2-(2,3-dihydroxypropyl)-7-methyl-octanoic acid isobutylamide (a) 81 mg of L-N-benzyloxycarbonylnaphthylalanyl-L-norleucine was dissolved in 0.6 ml of dry dimethylformamide, and 30 μl of triethylamine, 45 μl of diphenylphosphorylazide and a solution prepared by dissolving 67 mg of (2RS,4S,5S)-5-amino-4-hydroxy-2-(2,3-O-isopropylidenepropyl)-7-methyl-octanoic acid isobutylamide in 0.8 ml of dry dimethylformamide, were added thereto at −20° C. under stirring. The mixture was stirred overnight at room temperature, and then 20 ml of ethyl acetate was added thereto. The ethyl acetate layer was washed sequentially with a 10% citric acid aqueous solution, water, a 4% sodium hydrogencarbonate aqueous solution, water and a saturated sodium chloride aqueous solution and then dried over anhydrous magnesium sulfate. The solvent was distilled off under reduced pressure, and the residue was purified by silica gel column chromatography (4 g of Kieselgel 60) by using chloroform/methanol (40/1) to obtain 93 mg of (2RS,4S,5S)-5-(L-N-benzyloxycarbonylnaphthylalanyl-L-norleucyl)amino-4-hydroxy-2-(2,3-O-isopropylidenepropyl)-7-methyl-octanoic acid isobutylamide as a colorless powder.

$R_f$: 0.23 (silica gel plate, developer: chloroform/methanol (30/1))

(b) 93 mg of (2RS,4S,5S)-5-(L-N-benzyloxycarbonylnaphthylalanyl-L-norleucyl)amino-4-hydroxy-2-(2,3-O-isopropylidenepropyl)-7-methyl-octanoic acid isobutylamide was dissolved in 3.5 ml of a mixture of methanol/ethyl acetate (5/2), and 0.4 ml of 1N hydrochloric acid was added thereto under stirring. The mixture was stirred at room temperature for one hour, and then, 10 ml of water was added thereto. The aqueous layer was extracted three times with 20 ml of ethyl acetate. The ethyl acetate layer was washed sequentially with water and a saturated sodium chloride aqueous solution and then dried over anhydrous magnesium sulfate. Then, the solvent was distilled off under reduced pressure, and the residue was crystallized by using methanol/water to obtain 79 mg of the above-identified compound as a crystalline powder.

$R_f$: 0.19, 0.22 (silica gel plate, developer: chloroform/methanol (10/1))

Mass spectrum: m/z 763 (M$^+$+1)

EXAMPLE 17

(1) L-N-henoxyacetylphenylalanyl-L-histidine (a) 3.1 g of L-phenylalanine was dissolved in 30 ml of a mixture of dioxane/water (1/1), and 2.33 g of sodium carbonate was added thereto under stirring. The mixture was cooled to 0° C., and then 2.85 ml of phenoxyacetyl chloride was added thereto. The mixture was stirred at room temperature for 3 hours, and insolubles were filtered off. The filtrate was adjusted to pH 4 with 1N hydrochloric acid and then extracted once with 300 ml and once with 200 ml of ethyl acetate. The ethyl acetate layer dried over anhydrous magnesium sulfate. Then, the solvent was distilled off under reduced pressure to obtain 1.26 g of L-N-phenoxyacetylphenylalanine as a white solid substance. Further, the aqueous layer was again adjusted to pH 4 with 1N hydrochloric acid, and the precipitated desired product was collected by filtration to obtain 0.93 g of the compound. The filtrate was again adjusted to pH 4, followed by the same treatment to obtain 3.05 g of the same compound as precipitates.

(b) 1.16 g of L-N-phenoxyacetylphenylalanine was dissolved in 10 ml of dry dimethylformamide, and 0.65 ml of triethylamine, 1.0 ml of diphenylphosphorylazide and a mixture obtained by suspending 0.99 g of L-histidine methylester dihydrochloride in 10 ml of dry dimethylformamide (containing 1.14 ml of triethylamine), were added thereto at −15° C. under stirring. The mixture was stirred overnight at 5° C., and the solvent was distilled off under reduced pressure. The residue was dissolved in 200 ml of ethyl acetate and then washed sequentially with water, a potassium hydrogensulfate aqueous solution, a 4% sodium hydrogencarbonate aqueous solution, water and a saturated sodium chloride aqueous solution, and then dried over anhydrous magnesium sulfate. The solvent was distilled off under reduced pressure, and precipitated crystals were collected by filtration and washed with ethyl ether to obtain 300 mg of L-N-phenoxyacetylphenylalanyl-L-histidine methyl ester as a pale yellow solid. The solvent was distilled off from the filtrate under reduced pressure, and the residue was purified by silica gel column chromatography (Kieselgel 60) by using chloroform/methanol (30/1 to 5/1) to obtain 80 mg of the same compound.

$R_f$: 0.52 (silica gel plate, developer: chloroform/methanol (5/1))

(c) 203 mg of L-N-phenoxyacetylphenylalanyl-L-histidine methyl ester was dissolved in 1.0 ml of ethanol, and 1.2 ml of an ethanol/water (10/1) solution of 2N potassium hydroxide was added thereto under stirring. The mixture was stirred overnight at room temperature, then, cooled to 0° C. and neutralized with 1N hydrochloric acid. The solvent was distilled off from the reaction mixture under reduced pressure to obtain 96 mg of the above-identified compound as a pale yellow solid substance.

(2)
(2RS,4S,5S)-5-(L-N-phenoxyacetylphenylalanyl-L-histidyl)amino-4-hydroxy-2-(3-hydroxypropyl)-7-methyl-octanoic acid isobutylamide (a) 61 mg of L-N-phenoxyacetylphenylalanyl-L-histidine was dissolved in 0.5 ml of dry dimethylformamide, and 45 μl of triethylamine, 35 μl of diphenylphosphorylazide and a mixture obtained by dissolving 59 mg of (2RS,4S,5S)-5-amino-4-hydroxy-2-[3-(2-tetrahydropyranyloxy)propyl]-7-methyl-octanoic acid isobutylamide in 0.5 ml of dry dimethylformamide, were added thereto at −20° C. under stirring. The mixture was stirred at the same temperature for two hours and at 5° C. overnight and then concentrated under reduced pressure. Then, 20 ml of ethyl acetate was added. The ethyl acetate layer was washed sequentially with a 10% citric acid aqueous solution, water, a 4% sodium hydrogencarbonate aqueous solution, water and a saturated sodium chloride aqueous solution and then dried over anhydrous magnesium sulfate. Then, the solvent was distilled off under reduced pressure, and the residue was purified by silica gel column chromatography (4 g of Kieselgel 60) by using chloroform/methanol (20/1) to obtain 52 mg of (2RS,4S,5S)-5-(L-N-phenoxyacetylphenylalanyl-L-histidyl)amino-4-hydroxy-2-[3-(2-tetrahydropyranyloxy)-propyl]-7-methyl-octanoic acid isobutylamide as a colorless powder.

$R_f$: 0.63 (silica gel plate, developer: chloroform/methanol (5/1))

(b) 52 mg of (2RS,4S,5S)-5-(L-N-phenoxyacetylphenylalanyl-L-histidyl)amino-4-hydroxy-2-[3-(2-tetrahydropyranyloxy)propyl]-7-methyl-octanoic acid isobutylamide was dissolved in 2 ml of methanol, and then, 0.22 ml of 1N hydrochloric acid was added thereto under stirring. The mixture was stirred overnight at room temperature, and then 10 ml of water was added thereto. The aqueous layer was extracted twice with 20 ml of ethyl acetate. The ethyl acetate layer was washed sequentially with water and a saturated sodium chloride aqueous solution, and then dried over anhydrous magnesium sulfate. Then, the solvent was distilled off under reduced pressure, and precipitated crystals were washed with ethyl acetate to obtain 6 mg of the above-identified compound as colorless crystals. To the aqueous layer, sodium chloride was added, and precipitated crystals were collected by filtration to obtain 9 mg of the above-identified compound. Further, the filtrate was extracted twice with 20 ml of ethyl acetate. The ethyl acetate layer was dried over anhydrous magnesium sulfate. Then, the solvent was distilled off under reduced pressure to obtain 14 mg of the above-identified compound.

$R_f$: 0.45 (silica gel palte, developer: chloroform/methanol (5/1))

EXAMPLE 18

(1) Ethyl 2-diethylphosphono-4-(2-tetrahydropyranyloxy)pentanoate (a) 5.0 ml of 1-bromo-2-propanol was dissolved in 40 ml of dry dichloromethane, and 7.6 ml of 2,3-dihydropyran and 237 mg of dry p-toluenesulfonic acid were added thereto. The mixture was reacted at room temperature for 5 hours and then diluted by an addition of 250 ml of chloroform. The mixture was washed sequentially with a 4% sodium hydrogencarbonate aqueous solution and a saturated sodium chloride aqueous solution. Then, the chloroform layer was dried over anhydrous magnesium sulfate. After filtering the inorganic salt off, the filtrate was concentrated under reduced pressure to obtain a brown syrup. This syrup was purified by silica gel flash column chromatography (130 g of Wacogel C-300 and eluted with hexane/ethyl acetate (15/1). The eluate containing the desired product was collected and concentrated under reduced pressure to obtain 11.3 g of 1-bromo-2-(tetrahydropyran-2-yl)oxypropane as a colorless transparent volatile syrup.

NMR (60 MHz, CDCl$_3$, δ ppm): 1.0–2.0(9H, m), 3.2–4.8(5H, m), 4.7(1H, br)

$R_f$: 0.34 (silica gel plate, developer: hexane/ethyl acetate (15/1))

(b) 1.2 g of sodium hydride (60% in oil) was washed a few times with dry hexane and quickly dried by blowing an argon stream. After being dried completely, it is sealed under an argon stream. Then, 15 ml of dry dimethylformamide was added thereto, stirred and suspended. Then, 5.8 ml of ethyl diethylphosphono acetate was gradually dropwise added thereto under cooling with ice. The mixture was stirred at room temperature for 30 minutes. Then, a solution prepared by dissolving 9.7 g of 1-bromo-2-(tetrahydropyran-2-yl)oxypropane in 0.5 ml of dry dimethylformamide was gradually dropwise added again under cooling with ice. The ice bath was removed, and the mixture was stirred at room temperature for 10 minutes. Then, the stirring was continued at 45° C. overnight and at 55° C. for 4 hours. The reaction solution was diluted with 500 ml of water and extracted with 500 ml of ethyl acetate. The ethyl acetate extract thus obtained was washed with 500 ml of a saturated sodium chloride aqueous solution. The ethyl acetate layer was separated, then dried over anhydrous magnesium sulfate and concentrated under reduced pressure. A syrup thus obtained was purified by silica gel flash column chromatography (125 g of Wacogel C-300, developer: hexane/ethyl acetate (2/1 to 1/2)). Among the eluted fractions in which the desired product and the starting material were not separated, were put together, concentrated and again purified by silica gel flash chromatography (35 g of Wacogel C-300, developer: hexane/ethyl acetate (1/2)). The fractions containing the desired product obtained by the two operations of purification, were put together, concentrated and dried under reduced pressure to obtain 2.4 g of ethyl 2-diethylphosphono-4-(tetrahydropyran-2-yloxy)pentanoate.

$R_f$: 0.46 (silica gel plate, developer: hexane/ethyl acetate (1/5))

(2)
(2RS,4S,5S)-5-amino-4-hydroxy-2-[2-(2-tetrahydropyranyloxy)propyl]-7-methyl-octanoic acid isobutylamide (a) 68 mg of lithium chloride was suspended in 5 ml of dry tetrahydrofuran under an argon stream. Then, a solution prepared by dissolving 0.53 g of 2-diethylphosphono-4-(tetrahydropyran-2-yloxy)pentanoic acid in 1.0 ml of dry tetrahydrofuran, was dropwise added thereto under stirring. The mixture was stirred for 5 minutes, and 0.55 ml of a dry tetrahydrofuran solution of diazabicycloundecene (1/1) was gradually added thereto. The mixture was stirred at room temperature for 10 minutes. Then, a solution prepared by dissolving 385 mg of (4S,5S)-3-benzyloxycarbonyl-4-isobutyl-5-formyl-2,2-dimethyloxazolidine in 2.0 ml of dry tetrahydrofuran, was gradually dropwise added thereto. The mixture was stirred overnight at room temperature. Then, after filtering precipitated inorganic salt off, the reaction solution was neutralized with 1N hydrochloric acid. The reaction, solution was concentrated under reduced pressure, and a syrup thereby obtained was dissolved in 50 ml of benzene, then washed sequentially with 50 ml of water and 50 ml of a saturated sodium chloride aqueous solution and then dried over anhydrous magnesium sulfate. After filtering the inorganic salt off, the filtrate was concentrated under reduced pressure, and a syrup thereby obtained was purified by silica gel flash column chromatography (Kieselgel (E. Merck No. 9385), developer: hexane/ethyl acetate (10/1)). The fraction containing the desired product was concentrated and dried under reduced pressure to obtain 454 mg of ethyl 3-[(4S,5S)-3-benzyloxycarbonyl-4-isobutyl-2,2-dimethyloxazolidin-5-yl]-2-[2-(2-tetrahydropyranyloxy)-propyl]-2-pentenoate as a colorless transparent syrup.

NMR (60 MHz, CDCl$_3$, δ ppm): 0.6–1.0(6H, m), 1.0–1.9(21H, m), 2.5(2H, m), 3.2–4.1(4H, m), 4.2(2H, q, J=7 Hz), 4.6(1H, br), 5.1(2H, s), 6.00(0.5H, br), 6.8(0.5H, d, J=9 Hz)

Mass spectrum: 532(M$^+$+1), 530(M$^+$−1), 430, 390

$R_f$: 0.55 (silica gel plate, developer: hexane/ethyl acetate (3/1))

(b) 400 mg of ethyl 3-[(4S,5S)-3-benzyloxycarbonyl-4-isobutyl-2,2-dimethyloxazolidin-5-yl]-2-[2-(2tetrahydropyranyloxy)propyl]-2-pentenoate was dissolved in 1 ml of an ethanol/water (10/1) solution. Then, 1.9 ml of an ethanol aqueous solution (ethanol/water (10/1)) of 2N potassium hydroxide was added thereto, and the mixture was stirred overnight at room temperature. Then, the mixture was cooled to 0° C. and adjusted to pH5 with 1N hydrochloric acid. The reaction solution was diluted with 40 ml of water and then extracted with 50 ml of ethyl acetate. The ethyl acetate layer thus obtained was washed with 40 ml of a saturated sodium chloride aqueous solution and then dried over anhydrous magnesium sulfate. After filtering the inorganic salt off, the filtrate was concentrated and dried under reduced pressure to obtain a syrup of 3-[(4S,5S)-3-benzyloxycarbonyl-4-isobutyl-2,2-dimethyloxazolidin-5-yl]-2-[2-(2-tetrahydropyranyloxy)propyl]-2-pentanoic acid. This syrup was further dried under reduced pressure for a few hours and then dissolved in 5 ml of dry dimethylformamide, and then 0.14 ml of triethylamine was added thereto. The mixture was cooled to −15° C. Then, 0.21 ml of diphenylphosphorylazide was added to the reaction solution, and the mixture as stirred for 5 minutes. Then, 0.14 ml of isobutylamine was added thereto, and the mixture was stirred at −15° C. for one hour and then at 5° C. overnight. Then, the reaction solution was concentrated at room temperature under reduced pressure to obtain a syrup. The syrup was dissolved in 50 ml of benzene. The solution was washed sequentially with 40 ml of each of a 5% potassium hydrogensulfate aqueous solution, a 4% sodium hydrogencarbonate aqueous solution and a saturated sodium chloride aqueous solution. The organic layer was separated and dried over anhydrous magnesium sulfate. After filtering the in organic salt off, the filtrate was concentrated under reduced pressure, and a syrup thereby obtained was purified by silica gel flash column chromatography (Kieselgel (E. Merck Art. 9385), developer: hexane/ethyl acetate (3/1)). The eluted fraction containing the desired product was concentrated and dried under reduced pressure to obtain 310 mg of 3-[(4S,5S)-3-benzyloxycarbonyl-4-isobutyl-2,2-dimethyloxazolidin-5-yl]-2-[2-(2-tetrahydropyranyloxy)-propyl]-2-propenoic acid isobutylamide as a colorless transparent syrup.

Mass spectrum: m/z 559(M$^+$+1), 543(M$^+$−CH$_3$),

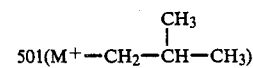

$501(M^+ -CH_2-\overset{\underset{\displaystyle |}{CH_3}}{CH}-CH_3)$ $R_f$: 0.27 (silica gel plate, developer: hexane/ethyl acetate (3/1))

(c) 254 mg of 3-[(4S,5S)-3-benzyloxycarbonyl-4-isobutyl-2,2-dimethyloxazolidin-5-yl]-2-[2-(2-tetrahydropyranyloxy)propyl]-2-propenoic acid isobutylamide was dissolved in 3 ml of ethanol. Then, a palladium black catalyst was added thereto, and hydrogen was continuously blown into the solution under atmospheric pressure for 4 hours. Then, the catalyst was filtered off, and a fresh palladium black catalyst was added. Then, hydrogen was continuously brown into the solution for further 4 hours. The catalyst was filtered off, and the reaction solution was concentrated and dried under reduced pressure to obtain 180 mg of (2RS,4S,5S)-5-amino-4-hydroxy-2-[2-(2-tetrahydropyranyloxy)-propyl]-7-methyl-octanoic acid isobutylamide as a solid substance.

Mass spectrum: m/z 387 (M$^+$+1), 343, 329, 303, 285

$R_f$: 0.35 and 0.43 (silica gel plate, developer: chloroform/methanol/concentrated ammonia (20/0.5/0.2))

(3)
(2RS,4S,5S)-5-(L-naphthylalanyl-L-norleucyl)amino-4-hydroxy-2-(2-hydroxypropyl)-7-methyl-octanoic acid isobutylamide monohydrochloride (a) 55 mg of L-N-benzyloxycarbonylnaphthylalanyl-L-norleucine was dissolved in 1 ml of dry dimethylformamide. Then, 0.02 ml of triethylamine and 0.04 ml of diphenylphosphorylazide were added thereto at −20° C. under stirring. 5 Minutes later, a dry dimethylformamide solution (0.5 ml×2) of 111 mg of (2RS,4S,5S)-5-amino-4-hydroxy-2-[2-(2-tetrahydropyranyloxy)propyl]-7-methyl-octanoic acid isobutylamide was added thereto at −20° C. under stirring. The mixture was stirred at −20° C. for one hour and then at 5° C. overnight. Then, the reaction solution was concentrated at room temperature under reduced pressure to obtain a syrup. The syrup was dissolved in 10 ml of ethyl acetate. The ethyl acetate layer was washed sequentially with 8 ml of each of a 5% potassium hydrogensulfate aqueous solution, a 4% sodium hydrogencarbonate aqueous solution and a saturated sodium chloride aqueous solution and then dried over anhydrous magnesium sulfate. After filtering the inorganic salt off, the filtrate was concentrated under reduced pressure to obtain a solid, which was then purified by silica gel column chromatography (10 g of Kieselgel (E. Merck Art. 7734), developer: chloroform/methanol (40/1)). The eluted fraction containing the desired product was concentrated and dried under reduced pressure to obtain 80 mg of (2RS,4S,5S)-5-(L-N-benzyloxycarbonylnaphthylalanyl-L-norleucyl)-amino-4-hydroxy-2-[2-(2-tetrahydropyranyloxy)propyl]-7-methyl-octanoic acid isobutylamide as a white solid substance.

$R_f$: 0.28 (silica gel plate, developer: chloroform/methanol (30/1))

(b) 80 mg of (2RS,4S,5S)-5-(L-N-benzyloxycarbonylnaphthylalanyl-L-norleucyl)amino-4-hydroxy-2-[2-(2-tetrahydropyranyloxy)propyl]-7-methyl-octanoic acid isobutylamide was dissolved in a mixture comprising 1 ml of methanol and 0.8 ml of ethyl acetate. Then, 2.0 ml of 1N hydrochloric acid was added thereto, and the mixture was reacted at room temperature for 2 hours to remove the tetrahydropyranyl group. The reaction solution was neutralized with a 1M sodium hydrogencarbonate aqueous solution under cooling with ice and concentrated under reduced pressure to obtain an aqueous solution. Then, 5 ml of cold water was added thereto, and precipitated crystals were aged under cooling with ice. The crystals were collected by filtration and dried under reduced pressure to obtain 68 mg of (2RS,4S,5S)-5-(L-N-benzyloxycarbonylnaphthylalanyl-L-norleucyl)amino-4-hydroxy-2-(2-hydroxypropyl)-7-methyl-octanoic acid isobutylamide.

NMR (300 MHz, CDCl$_6$, δ ppm): 2.5–2.9(1H, m), 3.08(2H, m), 3.48–4.7(5H), 4.16(1H, m), 4.51(1H, m), 5.05(2H, m)

Mass spectrum: m/z 747(M$^+$+1), 746(M$^+$−1)

$R_f$: 0.54, 0.60 (silica gel plate, developer: chloroform/methanol (10/1))

EXAMPLE 19

(2RS,4S,5S)-5-(L-naphthylalanyl-L-norleucyl)amino-4-hydroxy-2-(2-hydroxypropyl)-7-methyl-octanoic acid isobutylamide monohydrochloride 116 mg of (2RS,4S,5S)-5-(L-N-benzyloxycarbonylnaphthylalanyl-L-norleucyl)amino-4-hydroxy-2-(2-hydroxypropyl)-7-methyl-octanoic acid isobutylamide obtained in Example 5 was dissolved in 8 ml of methanol. A few mg of a palladium black catalyst was added thereto, and hydrogen was continuously blown into the solution for 5 hours. Then, the catalyst was filtered off, and 0.8 ml of 0.2N hydrochlolic acid was gradually dropwise added to the reaction solution under cooling with ice to bring the pH to 5. The reaction solution was concentrated under reduced pressure, and a syrup thereby obtained was dissolved in ethyl ether. The solution was concentrated to dryness under reduced pressure and further thoroughly dried under reduced pressure. The obtained solid was recrystallized from a mixture of methanol/ethyl ether/benzene. The crystals were collected by filtration and dried to obtain 73 mg of (2RS,4S,5S)-5-(L-naphthylalanyl-L-norleucyl)amino-4-hydroxy-2-(2-hydroxypropyl)-7-methyl-octanoic acid isobutylamide monohydrochloride as white crystals.

Mass spectrum: m/z 613 (M$^+$+1)

$R_f$: 0.41, 0.47 (silica gel plate, developer: chloroform/methanol (10/1))

EXAMPLE 20

(2RS,4S,5S)-5-(L-naphthylalanyl-L-norleucyl)amino-4-hydroxy-2-(2-hydroxyethyl)-7-methyl-octanoic acid isobutylamide monohydrochloride 18.9 mg of (2RS,4S,5S)-5-(L-N-benzyloxycarbonylnaphthylalanyl-L-norleucyl)amino-4-hydroxy-2-(2-hydroxyethyl)-7-methyl-octanoic acid isobutylamide was dissolved in 0.5 ml of methanol and then hydrogenated by using palladium black as a catalyst under atmospheric pressure. The reaction mixture was subjected to filtration, and the solvent of the filtrate was distilled off under reduced pressure to obtain 14.7 mg of (2RS,4S,5S)-5-(L-naphthylalanyl-L-norleucyl)amino-4-hydroxy-2-(2-hydroxyethyl)-7-methyl-octanoic acid isobutylamide. This product was dissolved in 1 ml of methanol, and 0.245 ml of 0.1N hydrochloric acid was added thereto. The solvent was distilled off under reduced pressure to obtain 15.3 mg of (2RS,4S,5S)-5-(L-naphthylalanyl-L-norleucyl)amino-4-hydroxy-2-(2-hydroxyethyl)-7-methyl-octanoic acid isobutylamide monohydrochloride as a colorless powder.

$R_f$: 0.33, 0.37 (silica gel plate, developer: chloroform/methanol (10/1))

EXAMPLE 21

(2RS,4S,5S)-5-(L-naphthylalanyl-L-norleucyl)amino-4-hydroxy-2-(3-hydroxypropyl)-7-methyl-octanoic acid isobutylamide monohydrochloride 20 mg of (2RS,4S,5S)-5-(L-N-benzyloxycarbonylnaphthylalanyl-L-norleucyl)amino-4-hydroxy-2-(3-hydroxypropyl)-7-methyl-octanoic acid isobutylamide was dissolved in 0.6 ml of ethanol and then hydrogenated in the presence of palladium black at room temperature under atmospheric pressure. The catalyst was filtered off, and the solvent was distilled off under reduced pressure. Then, 1.0 ml of methanol and 0.25 ml of 0.1N hydrochloric acid were added to the residue. The solvent was distilled off under reduced pressure, and the residue was crystallized from ethyl ether to obtain 15.7 mg of (2RS,4S,5S)-5-(L-naphthylalanyl-L-norleucyl)amino-4-hydroxy-2-(3-hydroxypropyl)-7-methyl-octanoic acid isobutylamide monohydrochloride as a colorless powder.

Rf: 0.08 (silica gel plate, developer: chloroform/methanol (20/1))

Mass spectrum: m/z 613 (M+ +1)

EXAMPLE 22

(2RS,4S,5S)-5-(L-naphthylalanyl-L-norleucyl)amino-4-hydroxy-2-(2,3-dihydroxypropyl)-7-methyl-octanoic acid isobutylamide monohydrochloride 21 mg of (2RS,4S,5S)-5-(L-N-benzyloxycarbonylnaphthylalanyl-L-norleucyl)amino-4-hydroxy-2-(2,3-dihydroxypropyl)-7-methyl-octanoic acid isobutylamide was dissolved in 1.0 ml of ethanol and then hydrogenated in the presence of palladium black at room temperature under atmospheric pressure. The catalyst was filtered off, and the solvent was distilled off under reduced pressure. 1.0 ml of methanol and 0.27 ml of 0.1N hydrochloric acid were added to the residue. The solvent was distilled off under reduced pressure, and the residue was crystallized from ethyl ether to obtain 18.8 mg of (2RS,4S,5S)-5-(L-naphthylalanyl-L-norleucyl)amino-4-hydroxy-2-(2,3-dihydroxypropyl)-7-methyl octanoic acid isobutylamide monohydrochloride as a colorless powder.

Rf: 0.17 (silica gel plate, developer: chloroform/methanol (10/1))

EXAMPLE 23

(2RS,4S,5S)-5-(L-N-methylnaphthylalanyl-L-norleucyl)amino-4-hydroxy-2-(2-hydroxypropyl)-7-methyl-octanoic acid isobutylamide (a) 17.1 mg of (2RS,4S,5S)-5-(L-naphthylalanyl-L-norleucyl)amino-4-hydroxy-2-(2-hydroxypropyl)-7-methyl-octanoic acid isobutylamide was dissolved in methanol, and 29.6 mg of benzaldehyde was added thereto at 0° C. under stirring. The mixture was stirred at room temperature for 1 hour. The mixture was cooled again to 0° C., and a methanol solution of 17.5 mg of sodium cyanoborohydride was added thereto. The pH of the reaction solution was adjusted to 5 with 0.1N hydrochloric acid, and the mixture was stirred at room temperature for 1 hour. The pH of the reaction solution was adjusted to 9 with a saturated sodium hydrogencarbonate aqueous solution, and the reaction solution was extracted with ethyl acetate. The ethyl acetate layer was washed with water and a saturated sodium chloride aqueous solution, and then the solvent was distilled off under reduced pressure. The residue thus obtained was purified by silica gel column chromatography (Kieselgel 60) by using a mixture of chloroform/methanol (20/1) to obtain 15.1 mg of (2RS,4S,5S)-5-(L-N-benzylnaphthylalanyl-L-norleucyl)amino-4-hydroxy-2-(2-hydroxypropyl)-7-methyl-octanoic acid isobutylamide.

Rf: 0.36, 0.27 (silica gel plate, developer: chloroform/methanol (10/1)

NMR(300 MHz, CDCl$_3$, δ ppm): 0.8–1.0(12H), 1.15–1.47(8H), 1.48–2.0(12H), 2.7(1H, m), 2.91–3.11(3H, m), 3.32(3H, m), 3.52–3.68(3H, m), 3.74–3.96(3H, m), 4.39(1H, m), 6.84(2H, m), 7.1(3H, m), 7.39(1H, t, J=7.5 Hz), 7.5(2H, m), 7.8(1H, d, J=8 Hz), 7.88(1H, m), 7.97(1H, m), 8.08(1H, m)

Mass spectrum: m/z 703 (M+ +1)

(b) 22 mg of (2RS,4S,5S)-5-(L-N-benzylnaphthylalanyl-L-norleucyl)amino-4-hydroxy-2-(2-hydroxypropyl)-7-methyl-octanoic acid isobutylamide was dissolved in methanol, and 30.7 μl of a 37% formaldehyde aqueous solution was added at room temperature under stirring. The mixture was stirred for 1 hour, and a methanol solution of 19.7 mg of sodium cyanoborohydride was added thereto. The pH of thereaction solution was adjusted to 4 with 0.1N hydrochloric acid at 0° C. The mixture was stirred at room temperature for 1.5 hours, and the pH of the reaction solution was adjusted to 2 with 8.7N acetic acid at 0° C. Then, the solution was adjusted to pH 9 with saturated sodium hydrogencarbonate aqueous solution and then extracted with ethyl acetate. The ethyl acetate layer was washed with water and a saturated sodium chloride aqueous solution and then dried over anhydrous sodium sulfate. Then, the solvent was distilled off under reduced pressure to obtain 20.1 mg of (2RS,4S,5S)-5-(L-N-methyl-N-benzylnaphthylalanyl-L-norleucyl)amino-4-hydroxy-2-(2-hydroxypropyl)-7-methyl-octanoic acid isobutylamide.

Rf: 0.39, 0.29 (silica gel plate, developer: chloroform/methanol (10/1))

Mass spectrum m/z 716 (M+), 739 (M+ +Na)

NMR (300 MHz, CDCl$_3$, δ ppm): 0.76–1.0(12H, m), 1.1–2.0(20H), 2.40–2.57(3H, m), 2.68(1H, m), 3.02(2H, m), 3.21–4.0(8H, m), 4.28(1H, m), 6.87(2H, m), 7.15(3H, m), 7.3–7.53(4H, m), 7.75(1H, m), 7.87(1H, m), 8.01(1H, m)

(c) 5.2 mg of (2RS,4S,5S)-5-(L-N-methyl-N-benzylnaphthylalanyl-L-norleucyl)amino-4-hydroxy-2-(2-hydroxypropyl)-7-methyl-octanoic acid isobutylamide was dissolved in methanol, and 73 μl of 0.1N hydrochloric acid was added thereto. The solution was hydrogenated by using palladium black under atmospheric pressure. The reaction mixture was subjected to filtration, and the solvent of the filtrate was distilled off under reduced pressure. The residue was purified by silica gel column chromatography (Kieselgel 60) by using a mixture of chloroform/methanol (10/1) to obtain 2.7 mg of (2RS,4S,5S)-5-(L-N-methylnaphthylalanyl-L-norleucyl)-amino-4-hydroxy-2-(2-hydroxypropyl)-7-methyl-octanoic acid isobutylamide.

Rf: 0.28, 0.25 (silica gel plate, developer: chloroform/methanol (10/1))

Mass spectrum: m/z 627 (M+ +1)

NMR (300 MHz, CDCl$_3$, δ ppm): 0.78–1.0(12H, m), 1.12–1.44(8H, m), 1.44–1.97(12H, m), 2.11–2.4(3H), 2.51–2.73(1H, m), 2.92–3.14(3H, m), 3.41(1H, m), 3.54–3.94(4H), 4.35(1H, m), 7.3(1H, m), 7.4(1H, m), 7.53(2H, m), 7.78(1H, m), 7.88(1H, m), 8.17(1H, m)

EXAMPLE 24

(2RS,4S,5S)-5-amino-4-hydroxy-2-[2-(2-tetrahydropyranyloxy)ethyl]-7-methyl-octanoic acid methylamide (a) 58.3 mg of ethyl 3-[(4S,5S)-3-benzyloxycarbonyl-4-isobutyl-2,2-diemthyloxazolidin-5-yl]-2-[2-(2-tetrahydropyranyloxy)ethyl]-2-propenoate was dissolved in 0.282 ml of an ethanol/water (10/1) solution of 2N potassium hydroxide, and the mixture was stirred overnight at room temperature. Then, 6 ml of water was added thereto and neutralized with 1N hydrochloric acid. After the neutralization, the mixture was extracted with ethyl acetate. The ethyl acetate layer was washed with water and a saturated sodium chloride aqueous solution and then dried over anhydrous sodium sulfate. The solvent was distilled off under reduced pressure to obtain 56 mg of 3-[(4S,5S)-3-benzyloxycarbonyl-4-isobutyl-2,2-dimethyloxazolidin-5-yl]-2-[2-(2-tetrahydropyranyloxy)ethyl]-2-propenoic acid as a colorless oily substance.

R$_f$: 0.39 (silica gel plate, developer: chloroform/methanol/acetic acid (10/0.5/0.1))

(b) 45 mg of 3-[(4S,5S)-3-benzyloxycarbonyl-4-isobutyl-2,2-dimethyloxazolidin-5-yl]-2-[2-(2-tetrahydropyranyloxy)ethyl]-2-propenoic acid was dissolved in 0.3 ml of dry dimethylformamide, and 3.71 mg of methylamide, 32.9 mg of diphenylphosphorylazide and 12.1 mg of triethylamine were added thereto at −10° C. under stirring. Then, the mixture was stirred at −10° C. for one hour and at room temperature overnight. To the reaction solution, 20 ml of ethyl acetate was added. The ethyl acetate layer was washed sequentially with a 10% citric acid aqueous solution, water, a 4% sodium hydrogencarbonate aqueous solution, water and a saturated sodium chloride aqueous solution and then dried over anhydrous sodium sulfate. The solvent was distilled off under reduced pressure, and the residue was purified by silica gel column chromatography (Kieselgel 60) by using a mixture of chloroform/methanol (5/1) to obtain 17.5 mg of 3-[(4S,5S)-3-benzyloxycarbonyl-4-isobutyl-2,2-dimethyloxazolidin-5-yl]-2-[2-(2-tetrahydropyranyloxy)ethyl]-2-propenoic acid methylamide as a colorless oily substance.

R$_f$: 0.34, 0.25 (silica gel plate, developer: chloroform/ethyl acetate (5/2))

NMR (60 MHz, CDCl$_3$, δ ppm): 0.65-1.0(6H, m), 1.19-1.81(15H), 2.15-2.7(2H), 2.81(3H, m), 3.17-4.02(5H), 4.4-4.7(2H, m), 5.1(2H, S), 5.74(0.5H, d, J=9 Hz), 6.5(0.5H, d, J=9 Hz), 6.7(1H, m), 7.3(5H, s)

(c) 29.2 mg of 3-[(4S,5S)-3-benzyloxycarbonyl-4-isobutyl-2,2-dimethyloxazolidin-5-yl]-2-[2-(2-tetrahydropyranyloxy)ethyl]-2-propenoic acid methylamide was dissolved in ethanol and then hydrogenated by using palladium black as a catalyst under atmospheric pressure. The reaction mixture was subjected to filtration, and the solvent of the filtrate was distilled off under reduced pressure to obtain 19.2 mg of (2RS,4S,5S)-5-amino-4-hydroxy-2-[2-(2-tetrahydropyranyloxy)ethyl]-7-methyl-octanoic acid methylamide.

R$_f$: 0.32 (silica gel plate, developer: chloroform/methanol/aqueous ammonia (10/0.5/0.2))

(2)
(2RS,4S,5S)-5-(L-N-benzyloxycarbonylnaphthylalanyl-L-norleucyl)amino-4-hydroxy-2-(2-hydroxyethyl)-7-methyl-octanoic acid methylamide (a) 19.2 mg of (2RS,4S,5S)-5-amino-4-hydroxy-2-[2-(2-tetrahydropyranyloxy)ethyl]-7-methyl-octanoic acid methylamide was dissolved in dry dimethylformamide, and L-norleucine, 19.2 mg of diphenylphosphorylazide and 7.05 mg of triethylamine were added at −10° C. under stirring. The mixture was stirred at the same temperature for one hour and at room temperature overnight. Then, 15 ml of ethyl acetate was added to the reaction solution. The ethyl acetate layer was washed sequentially with a 10% citric acid aqueous solution, water, a 4% sodium hydrogencarbonate aqueous solution, water and a saturated sodium chloride aqueous solution and then dried over anhydrous sodium sulfate. The solvent was distilled off under reduced pressure, and the residue was purified by silica gel column chromatography (Kieselgel 60) by using a mixture of chloroform/methanol (30/1) to obtain 15 mg of (2RS,4S,5S)-5-(L-N-benzyloxycarbonylnaphthylalanyl-L-norleucyl)amino-4-hydroxy-2-[2-(2-tetrahydropyranyloxy)ethyl]-7-methyl-octanoic acid methylamide.

R$_f$: 0.53 (silica gel plate, developer: chloroform/methanol (10/1)

(b) 15 mg of (2RS,4S,5S)-5-(L-N-benzyloxycarbonylnaphthylalanyl-L-norleucyl)amino-4-hydroxy-2-[2-(2-tetrahydropyranyloxy)ethyl]-7-methyl-octanoic acid methylamide was dissolved by an addition of 0.9 ml of methanol, 0.6ml of ethyl acetate and 0.3 ml of chloroform, and then 0.2 ml of 1N hydrochloric acid was added thereto. The mixture was stirred at room temperature for 2 hours. The reaction solution was poured into 10 ml of water and extracted with ethyl acetate. The ethyl acetate layer was washed with water and a saturated sodium chloride aqueous solution and then dried over anhydrous sodium sulfate. The solvent was distilled off under reduced pressure, and the residue was crystallized from methanol/water to obtain 9.2 mg of (2RS,4S,5S)-5-(L-N-benzyloxycarbonylnaphthylalanyl-L-norleucyl)amino-4-hydroxy-2-(2-hydroxyethyl)-7-methyl-octanoic acid methylamide as a colorless powder.

R$_f$: 0.28, 0.22 (silica gel plate, developer: chloroform/methanol (10/1))

Mass spectrum: m/z 691 (M$^+$+1), 713 (M$^+$+Na)

NMR (300 MHz, CD$_3$OD, δ ppm): 0.79-0.97(9H, m), 1.1-1.87(13H, m), 2.02(0.5H, m), 2.24(0.5H, m), 2.68(3H, s), 3.38-3.95(6H, m), 4.3(1H, m), 4.56(1H, m), 4.95 2H, s), 7.11-7.4(7H, m), 7.5(1H, m), 7.75(1H, m), 7.86(1H, d, J=8 Hz), 8.2(1H, d, J=8 Hz)

EXAMPLE 25

Sodium (2RS,4S,5S)-5-(L-N-benzyloxycarbonylnaphthylalanyl-L-norleucyl)amino-4-hydroxy-2-(2-hydroxyethyl)-7-methyl-octanoate (a) 50 mg of ethyl 3-[(4S,5S)-3-benzyloxycarbonyl-4-isobutyl-2,2-dimethyloxazolidin-5-yl -2-[2-(2-tetrahydropyranyloxy)ethyl]-2-propenoate was dissolved in 1.0 ml of ethanol and then hydrogenated in the presence of palladium black at room temperature under atmospheric pressure. The catalyst was filtered off, and the solvent was distilled off under reduced pressure to obtain 31 mg of amine as a colorless oily substance.

(b) 39 mg of L-N-benzyloxycarbonylnaphthylalanyl-L-norleucine was dissolved in 0.3 ml of dry dimethylformamide, and 16 μl of triethylamine, 25 μl of diphenylphosphorylazide and a solution obtained by dissolving 31 mg of the amine prepared in step (a) in 0.4 ml of dry dimethylformamide, were added thereto at −15° C. under stirring. The mixture was stirred overnight at room temperature. Then, 20 ml of ethyl acetate was added to the reaction mixture. The mixture was washed sequentially with a 10% citric acid aqueous solution, water, a 4% sodium hydrogencarbonate aqueous solution, water and a saturated sodium chloride aqueous solution. The ethyl acetate layer was dried over anhydrous magnesium sulfate, and the solvent was distilled off under reduced pressure to obtain 67 mg of a coupling compound as a colorless powder.

(c) 62 mg of the coupling compound was dissolved in 2.0 ml of methanol, and 0.22 ml of 1N hydrochloric acid was added thereto. The mixture was stirred at room temperature for 2 hours. The reaction mixture was poured into water and extracted with ethyl acetate. The ethyl acetate layer was washed with water and a saturated sodium chloride aqueous solution and then dried over anhydrous magnesium sulfate. Then, the solvent was distilled off under reduced pressure, and the residue was dissolved in 0.5 ml of dioxane. Then, 0.2 ml of water and 50 μl of 1N sodium hydroxide were added thereto, and the mixture was stirred overnight at room temperature. Then, the solvent was distilled off under reduced pressure, and the residue was crystallized from methanol/water to obtain 23.4 mg of sodium (2RS,4S,5S)-5-(L-N-benzyloxycarbonylnaphthylalanyl-L-norleucyl)amino-4-hydroxy-2-(2-hydroxyethyl)-7-methyloctanoate as a colorless powder.

$R_f$: 0.09 (silica gel plate, developer: chloroform/methanol/acetic acid (10/1/0.1))

Mass spectrum: m/z 700 (M+ +1)

NMR (300 MHz, DMSO-d$_6$, δ ppm): 0.76–0.92(9H, m), 1.12–1.77(13H, m), 2.03–2.13(0.7H, m), 2.24–2.37(0.3H, m), 3.03–3.48(4H, m), 3.48–3.6(1H, m), 3.66–3.84(1H, m), 4.26–4.5(2H, m), 4.88(2H, s), 7.11–8.23(12H)

EXAMPLE 26

3-[(4S,5S)-3-benzyloxycarbonyl-4-isobutyl-2,2-dimethyloxazolidin-5-yl]-2-[2-(2-tetrahydropyranyloxy)ethyl]-2-propenoic acid 4-picolylamide 98 mg of 3-[(4S,5S)-3-benzyloxycarbonyl-4-isobutyl-2,2-dimethyloxazolidin-5-yl]-2-[2-(2-tetrahydropyranyloxy)ethyl]-2-propenoic acid was dissolved in 0.4 ml of dry dichloromethane, and 21 μl of 4-picolylamine, 30 mg of 1-hydroxybenzotriazole and 45 mg of N,N'-dicyclohexylcarbodiimide were added thereto at 0° C. under stirring. The mixture was stirred at 0° C. for 2 hours and then at room temperature overnight. Insolubles were filtered off, and 20 ml of ethyl acetate was added. The mixture was washed with a saturated sodium hydrogencarbonate aqueous solution. The ethyl acetate layer was dried over anhydrous sodium sulfate, and then the solvent was distilled off under reduced pressure. The residue was purified by silica gel column chromatography (2 g of Kieselgel 60) by using chloroform/methanol (20/1) to obtain 121 mg of 3-[(4S,5S)-3-benzyloxycarbonyl-4-isobutyl-2,2-dimethyloxazolidin-5-yl]-2-[2-(2-tetrahydropyranyloxy)ethyl]-2-propenoic acid 4-picolylamide as a colorless oily substance.

$R_f$: 0.36, 0.42 (silica gel plate, developer: chloroform/methanol (20/1))

EXAMPLE 27

(2RS,4S,5S)-5-(L-N-benzyloxycarbonylnaphthylalanyl-L-methyl-octanoic acid 4-picolylamide (a) 61.8 mg of 3-[(4S,5S)-3-benzyloxycarbonyl-4-isobutyl-2,2-dimethyloxazolidin-5-yl]-2-[2-(2-tetrahydropyranyloxy)ethyl]-2-propenoic acid 4-picolylamide was dissolved in 1.0 ml of ethanol and then hydrogenated in the presence of palladium black at room temperature under atmospheric pressure. The catalyst was filtered off, and the solvent was distilled off under reduced pressure to obtain 34 mg of (2RS,4S,5S)-5-amino-4-hydroxy-2-[2-(2-tetrahydropyranyloxy)ethyl]-2-propenoic acid 4-picolylamide as a colorless oily substance.

$R_f$: 0.36 (silica gel plate, developer: chloroform/methanol/aqueous ammonia (10/1/0.1)

(b) 28.9 mg of L-N-benzyloxycarbonylnaphthylalanyl-L-norleucine was dissolved in 0.3 ml of dry dimethylformamide, and 13 μl of triethylamine, 20 μl of diphenylphosphorylazide and a solution prepared by dissolving 34 mg of (2RS,4S,5S)-5-amino-4-hydroxy-2-[2-(2-tetrahydropyranyloxy)ethyl]-2-propenoic acid 4-picolylamide in 0.4 ml of dry dimethylformamide, were added at −15° C. under stirring. The mixture was stirred overnight at room temperature. Then, 20 ml of ethyl acetate was added to the reaction mixture. The mixture was washed sequentially with a 10% citric acid aqueous solution, water, a 4% sodium hydrogencarbonate aqueous solution, water and a saturated sodium chloride aqueous solution. The ethyl acetate layer was dried over anhydrous magnesium sulfate, and the solvent was distilled off under reduced pressure to obtain 53 mg of a coupling compound. This coupling compound was dissolved in 1.2 ml of a mixture of methanol/ethyl acetate (5/1), and 156 μl of 1N hydrochloric acid was added thereto. The mixture was stirred at room temperature for 3 hours. The reaction mixture was poured into water and extracted with ethyl acetate. The ethyl acetate layer was washed with water and saturated sodium chloride aqueous solution and then dried over anhydrous magnesium sulfate. Then, the solvent was distilled off under reduced pressure, and the residue was purified by silica gel column chromatography (3 g of Kieselgel 60) by using chloroform/methanol (30/1) to obtain 8.2 mg of (2RS,4S,5S)-5-(L-N-benzyloxycarbonylnaphthylalanyl-L-norleucyl)amino-4-hydroxy-2-(2-hydroxyethyl)-7-methyl-octanoic acid 4-picolylamide as a colorless powder.

$R_f$: 0.23 (silica gel plate, developer: chloroform/methanol (10/1)

NMR(300 MHz, CDCl$_3$, δ ppm): 0.82 (3H, t, J=7.9 Hz), 0.86–1.03(6H, m), 1.1–1.71(13H, m), 2.58–2.84(1H, m), 3.3(1H, dd, J=14.2, 7.9 Hz), 3.49(1H, dd, J=14.2, 6.3 Hz), 3.64–3.81(1H, m) 3.85–4.05(1H, m), 4.2–4.45(1H, m), 4.46(1H, dd, J=15.8, 6.3 Hz), 4.61(1H, dd, J=15.8, 6.3 Hz), 5.0(1H, d, J=11.8 Hz), 5.11(1H, d, J=11.8 Hz), 5.22(1H, d, J=1.6 Hz), 6.01(1H, bd, J=3.9 Hz), 6.22(1H, d, J=7.9 Hz), 6.48(1H, d, J=7.9 Hz), 7.16–7.59(10H, m), 7.81(1H, d, J=7.9 Hz), 7.89(2H, d, J=7.9 Hz), 8.0(1H, bt) 8.52(2H, d, J=6.3 Hz)

REFERENCE EXAMPLE 1

(2RS,4S,5S)-5-amino-4-hydroxy-2-isopropyl7-methyl-octanoic acid isobutylamide (a) 123 mg of lithium chloride was suspended in 10 ml of dry tetrahydrofuran under an argon stream, and 0.69 ml of ethyl 2-diethylphosphono-3-methylbutanoate was added under stirring. The mixture was stirred for 5 minutes at room temperature, and then 2.7 ml of a 20% dry tetrahydrofuran solution of diazabicycloundecene was added thereto. The mixture was stirred at room temperature for 10 minutes. Then, 2.0 ml of a dry tetrahydrofuran solution of 773 mg of (4S,5R)-3-benzyloxycarbonyl-2,2-dimethyl-5-formyl-4-isobutyloxazolidine was added thereto, and the mixture was stirred overnight at room temperature. A precipitated inorganic salt was filtered off, and the solvent of the filtrate was distilled off under reduced pressure. The residue was dissolved in 300 ml of benzene and washed with 200 ml of water. The separated aqueous layer was extracted with 75 ml of benzene. The organic solvent layer thus obtained was dried over anhydrous magnesium sulfate. Then, the solvent was distilled off under reduced pressure, and the residue was purified by silica gel column chromatography (32 g of Kieselgel 60) by using a mixture of hexane/ethyl acetate (10/1) to obtain 623 mg of ethyl 3-[(4S,5S)-3-benzyloxycarbonyl-2,2-dimethyl-4-isobutyloxazolidin-5-yl]-2-isopropyl-2-propenoate as a colorless oily substance.

R$_f$: 0.31 (silica gel plate, developer: benzene/ethyl acetate (30/1))

Mass spectrum: m/z 432 (M$^+$+1)

(b) 199 mg of ethyl 3-[(4S,5S)-3-benzyloxycarbonyl-2,2-dimethyl-4-isobutyloxazolidin-5-yl]-2-isopropyl-2-propenoate was dissolved in 1.16 ml of an ethanol/water (10/1) solution of 2N potassium hydroxide, and the mixture was stirred overnight at room temperature. The mixture was cooled to 0° C. and adjusted to pH 2 with 1N hydrochloric acid, and then 12 ml of water was added thereto. The mixture was extracted 3 times with 10 ml of ethyl acetate. The organic solvent layer was washed sequentially with water and a saturated sodium chloride aqueous solution and then dried over anhydrous sodium sulfate. Then, the solvent was distilled off under reduced pressure to obtain 3-[(4S,5S)-3-benzyloxycarbonyl-2,2-dimethyl-4-isobutyloxazolidin-5-yl]-2-isopropyl-2-propenoic acid as a colorless oily substance.

Without purification, this propenoic acid was dissolved in 0.5 ml of dry dimethylformamide, and 54 μl of isobutylamine, 119 μl of diphenylphosphorylazide and 77 μl of triethylamine were added thereto at −10° C. under stirring. Then, the mixture was stirred at −10° C. for one hour and then at room temperature overnight. Then, 30 ml of ethyl acetate was added thereto. The organic solvent layer was washed sequentially with a 10% citric acid aqueous solution, water, a 4% sodium hydrogencarbonate aqueous solution, water and a saturated sodium chloride aqueous solution and then dried over anhydrous magnesium sulfate. Then, the solvent was distilled off under reduced pressure, and the residue was purified by silica gel column chromatography (24 g of Kieselgel 60) by using a mixture of hexane/ethyl acetate (5/1) to obtain 108 mg (Z-isomer: 74.4 mg, E-isomer: 33.6 mg) of 3-[(4S,5S)-3-benzyloxycarbonyl-2,2-dimethyl-4-isobutyloxazolidin-5-yl]-2-isopropyl-2-propenoic acid isobutylamide.

R$_f$: 0.51, 0.57 (silica gel plate, developer: hexane/ethyl acetate (5/2))

(c) 93 mg (Z-isomer) of 3-[(4S,5S)-3-benzyloxycarbonyl-2,2-dimethyl-4-isobutyloxazolidin-5-yl]-2-isopropyl-2-propenoic acid isobutylamide was dissolved in 0.8 ml of ethanol and then hydrogenated by using palladium black at atmospheric pressure. The reaction mixture was subjected to filtration, the solvent of the filtrate was distilled off under reduced pressure to obtain 58 mg of (2RS,4S,5S)-5-amino-4-hydroxy-2-isopropyl-7-methyl-octanoic acid isobutylamide as a colorless oily substance.

R$_f$: 0.27 (silica gel plate, developer: chloroform/methanol/aqueous ammonia (10/0.5/0.2))

REFERENCE EXAMPLE 2

(2RS,4S,5S)-5-(L-N-benzyloxycarbonyl-naphthylalanyl-L-norleucyl)amino-4-hydroxy-2-isopropyl-7-methyl-octanoic acid isobutylamide 58 mg of (2RS,4S,5S)-5-amino-4-hydroxy-2-isopropyl-7-methyl-octanoic acid isobutylamide was dissolved in 0.5 ml of dry dimethylformamide, and 93 mg of L-N-benzyloxycarbonylnaphthylalanyl-L-ncrleucine, 52 μl of diphenylphosphorylazide and 34 μl of triethylamine were added thereto at −10° C. under stirring. The mixture was stirred at −10° C. for one hour and then at room temperature overnight. Water was added to the reaction solution, and precipitates were collected by filtration. A colorless powder thus obtained was purified by silica gel column chromatography (10 g of Kieselgel 60) by using a mixture of chloroform/methanol (40/1), whereby 12.6 mg of (2R or 2S,4S,5S)-5-(L-N-benzyloxycarbonylnaphthylalanyl-L-norleucyl)amino-4-hydroxy-2-isopropyl-7-methyl-octanoic acid isobutylamide (R$_f$: 0.31), 51.8 mg of (2RS,4S,5S)-5-(L-N-benzyloxycarbonylnaphthylalanyl-L-norleucyl)amino-4-hydroxy-2-isopropyl-7-methyl-octanoic acid isobutylamide and 5.7 mg of (2S or 2R,4S,5S)-5-(L-N-benzyloxycarbonylnaphthylalanyl-L-norleucyl)amino-4-hydroxy-2-isopropyl-7-methyl-octanoic acid isobutylamide (R$_f$: 0.27) were obtained, respectively, as colorless powders.

R$_f$: 0.27, 0.31 (silica gel plate, developer: chloroform/methanol (20/1))

Mass spectrum: m/z (R$_f$: 0.27 substance) 732 (M$^+$), (R$_f$: 0.31 substance) 733 (M$^+$+1)

NMR (300 MHz, CD$_3$OD, δ ppm): R$_f$: 0.31 substance 0.8–1.0(18H, m), 1.23–1.42(7H, m), 1.45–1.88(9H, m), 2.13–2.26(1H, m),2.84–3.08(2H, m), 3.62–3.74(1H, m), 3.7–3.9(1H, m), 4.25–4.35(1H, m), 4.5–4.6(1H, m), 4,96(2H, s), 7.13–7.42(7H, m), 7.43–7.57(2H, m), 7.75(1H, dd, J=4.4, 6.0 Hz), 7.86(1H, d, J=8.1 Hz), 8.18(1H, d, J=8.7 Hz), R$_f$: 0.27 substance 0.85–1.0(18H, m), 1.18–1.42(7H, m), 1.53–1.87(9H, m), 1.97–2.08(1H, m), 2.85–3.05(2H, m), 3.4–3.5(1H, m), 3.64–3.75(1H, m), 3.9–4.0(1H, m), 4.3–4.38(1H, m), 4.53–4.63(1H, m), 4.95(2H, s), 7.15–7.41(7H, m), 7.43–7.57(2H, m), 7.75(1H, dd, J=2.1, 7.3 Hz), 7.85(1H, d, J=8.1 Hz), 8.19(1H, d, J=8.6 Hz)

Among the compounds of the present invention, those represented by the formula I have strong renin-inhibiting activities against a renin-angiotensin hypertensive system and thus expected to be useful as curing agents of hypertension due to the progress of the renin-angiotensin system. Further, the compounds represented by the formulas III and IV and the process using them are useful for the efficient production of the compounds having the renin-inhibiting activities.

We claim:

1. A 5-substituted amino-4-hydroxy-pentanoic acid derivative having the formula:

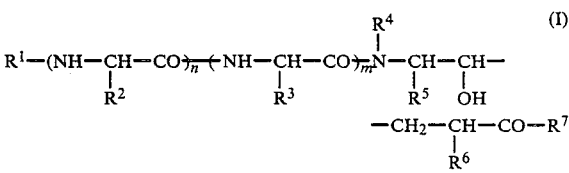

wherein

R$^1$ is a hydrogen atom, a lower alkoxycarbonyl group, an aryloxycarbonyl group, an aralkyloxycarbonyl group or a lower alkanoyl group which is unsubstituted or substituted by from one to three substituents selected from the group consisting of an amino group, a hydroxyl group, a carbonyl group, an aryloxy group, an aralkyloxycarbonylamino group, a lower alkoxycarbonylamino group and a

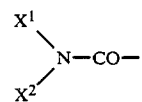

group wherein each of $X^1$ and $X^2$, which is the same or different, is a hydrogen atom, a lower alkyl group, an aryl group or an aralkyl group, or $X^1$ and $X^2$ together with the adjacent nitrogen atom from a 5- or 6-membered heterocyclic ring which contains no additional hetero atom or contains an additional hetero atom selected from the group consisting of a nitrogen atom, an oxygen atom and a sulfur atom, and wherein said alkanoyl group is saturated or contains a double bond in the carbon chain thereof, each of $R^2$, $R^3$ and $R^5$, which is the same or different, is a hydrogen atom, a lower alkyl group or a side chain of an acidic, neutral or basic amino acid selected from the group consisting of alanine, arginine, histidine, homoserine, leucine, naphthylalanine, norleucine, lysine, norvaline, ornithine, serine, threonine, throsine, valine, aspartic acid, glutamic acid, tryptophan, isoleucine, phenylalanine and cysteine, $R^4$ is a hydrogen atom or a lower alkyl group, $R^6$ is a lower alkyl, cycloalkyl, or cycloalkylalkyl which is substituted by one or two hydroxyl groups, $R^7$ is a hydroxyl group, a —OY group wherein Y is a lower alkyl group, an aryl group, an aralkyl group, a lower alkoxyalkyl group, a lower alkanoyloxyalkyl group, a lower alkoxycarbonyloxyalkyl group or a 1-phthalidyl group, or a

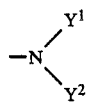

group wherein each of $Y^1$ and $Y^2$, which may be the same or different, is a hydrogen atom, a lower alkyl group, an aryl group, an aralkyl group or a cycloalkyl group, or $Y^1$ and $Y^2$ together with the adjacent nitrogen atom form a 5- or 6-membered heterocyclic ring which contains no additional hetero atoms or contains an additional hetero atom selected from the group consisting of a nitrogen atom, an oxygen atom and a sulfur atom, and each of n and m, which is the same or different, is 0 or 1.

2. The pentanoic acid derivative according to claim 1, which is (2RS,4S,5S)-5-(L-N-benzyloxycarbonylnaphthyl alanyl-L-norleucyl)amino-4-hydroxy-2-(3-hydroxypropyl)-7-methyl-octanoic acid isobutylamide, (2RS,4S,5S)-5-(L-N-benzyloxycarbonylnaphthylalanyl-L-norleucyl)amino-4-hydroxy-2-(2-hydroxyethyl)-7-methyl-octanoic acid isobutylamide, (2RS,4S,5S)-5-(L-N-benzyloxycarbonylnaphthylalanyl-L-norleucyl)amino-4-hydroxy-2-(2-hydroxypropyl)-7-methyl-octanoic acid isobutylamide, (2RS,4S,5S)-5-(L-naphthylalanyl-L-norleucyl)amino-4-hydroxy-2-(3-hydroxypropyl)-7-methyl-octanoic acid isobutylamide, (2RS,4S,5S)-5-(L-naphthylalanyl-L-norleucyl)amino-4-hydroxy-2-(2-hydroxyethyl)7-methyl-octanoic acid isobutylamide, (2RS,4S,5S)-5-(L-naphthylalanyl-L-norleucyl)amino-4-hydroxy-2-(2,3-dihydroxypropyl)-7-methyl-octanoic acid isobutylamide, (2RS,4S,5S)-5-(L-naphthylalanyl-L-norleucyl)amino-4-hydroxy-2-(2-hydroxypropyl)-7-methyl-octanoic acid isobutylamide, (2RS,4S,5S)-5-(L-N-methylnaphthylalanyl-L-norleucyl)amino-4-hydroxy-2-(2-hydroxypropyl)-7-methyl-octanoic acid isobutylamide, (2RS,4S,5S)-5-(L-N-benzyloxycarbonyl naphthylalanyl-L-norleucyl)amino-4-hydroxy-2-(2-hydroxyethyl)-7-methyl-octanoic acid methylamide, or (2RS,4S,5S)-5-(L-N-benzyloxycarbonyl naphthylalanyl-L-norleucyl)amino-4-hydroxy-2-(2-hydroxyethyl)-7-methyl-octanoic acid 4-picolylamide.

3. A hypotensive drug comprising an effective amount of a 5-substituted amino-4-hydroxy-pentanoic acid derivative of the formula I as defined in claim 1 and a pharmaceutically acceptable carrier.

* * * * *